US009895487B2

(12) United States Patent
Duncan

(10) Patent No.: US 9,895,487 B2
(45) Date of Patent: Feb. 20, 2018

(54) COMPACT NON-ELECTRIC MEDICAMENT INFUSER

(71) Applicant: David R. Duncan, Penryn, CA (US)

(72) Inventor: David R. Duncan, Penryn, CA (US)

( * ) Notice: Subject to any disclaimer, the term of this patent is extended or adjusted under 35 U.S.C. 154(b) by 177 days.

(21) Appl. No.: 14/357,035

(22) PCT Filed: Nov. 8, 2012

(86) PCT No.: PCT/US2012/000550
§ 371 (c)(1),
(2) Date: May 8, 2014

(87) PCT Pub. No.: WO2013/070259
PCT Pub. Date: May 16, 2013

(65) Prior Publication Data
US 2014/0323970 A1    Oct. 30, 2014

Related U.S. Application Data

(60) Provisional application No. 61/628,915, filed on Nov. 8, 2011.

(51) Int. Cl.
*A61M 5/145*    (2006.01)
*A61M 5/165*    (2006.01)
(Continued)

(52) U.S. Cl.
CPC .......... *A61M 5/145* (2013.01); *A61M 5/1454* (2013.01); *A61M 5/14526* (2013.01);
(Continued)

(58) Field of Classification Search
CPC .............. A61M 5/16827; A61M 5/315; A61M 5/31505; A61M 5/3137; A61M 5/31501;
(Continued)

(56) References Cited

U.S. PATENT DOCUMENTS 3,747,812 A * 7/1973 Karman ............... A61B 5/1405
                                                    222/387
4,180,067 A    12/1979 Derlien
(Continued)

FOREIGN PATENT DOCUMENTS

EP    0715861    6/1996
EP    0916353    5/1999
(Continued)

*Primary Examiner* — Nathan R Price
*Assistant Examiner* — Justin L Zamory
(74) *Attorney, Agent, or Firm* — Heisler & Associate

(57) ABSTRACT

An assembly is provided which includes an infusion device coupled to a standard medication syringe. The medication syringe may be coupled to a stopcock valve having multiple ports and to which syringes, vial adapters, infusion tubing, and multiple other items may be coupled. The infusion device includes a source of power based on a resistance force such as vacuum, spring or gas power. The infusion device converts the resistance based force to usable work in the form of a force applicator. The force applicator includes a driver section on one section of a reciprocating arm and an attachment to the power source on another section of the arm. The driver is pulled outward (excursion) to increase the size of the chamber, creating a force that tends to return the driver back inward, causing incursion. The driver can be attached removably to the syringe plunger to induce the infusion process.

27 Claims, 22 Drawing Sheets

(51) Int. Cl.
 A61M 5/315 (2006.01)
 A61M 39/22 (2006.01)
 A61M 5/19 (2006.01)
 A61M 5/20 (2006.01)
(52) U.S. Cl.
 CPC .............. *A61M 5/165* (2013.01); *A61M 5/19* (2013.01); *A61M 5/20* (2013.01); *A61M 5/2053* (2013.01); *A61M 5/315* (2013.01); *A61M 39/22* (2013.01)
(58) Field of Classification Search
 CPC ................ A61M 5/19; A61M 5/14216; A61M 5/14526; A61M 5/1424; A61M 2005/2073; A61M 2005/2086; A61M 2005/14204; B62K 21/08; B60G 15/12; B60G 13/06; F16F 9/0209; F16F 9/28; F16F 9/0218; F16F 9/062; F16F 9/5126; F16F 9/504
 See application file for complete search history.

(56) References Cited

U.S. PATENT DOCUMENTS

| | | | | |
|---|---|---|---|---|
| 4,711,637 | A * | 12/1987 | Leigh | A61B 10/0233 604/220 |
| 4,966,585 | A | 10/1990 | Gangemi | |
| 5,024,664 | A * | 6/1991 | Mitchell | A61M 5/14526 604/131 |
| 5,059,182 | A | 10/1991 | Laing | |
| 5,135,500 | A | 8/1992 | Zdeb | |
| 5,242,408 | A * | 9/1993 | Jhuboo | A61M 5/1456 604/121 |
| 5,290,259 | A * | 3/1994 | Fischer | A61M 5/19 222/137 |
| 5,807,337 | A | 9/1998 | Yamada | |
| 5,810,202 | A | 9/1998 | Hoback | |
| 6,056,724 | A | 5/2000 | Lacroix | |
| 6,139,530 | A | 10/2000 | Heijima | |
| 6,283,943 | B1 | 9/2001 | Dy | |
| 6,530,906 | B2 * | 3/2003 | Hu | A61M 5/322 128/919 |
| 6,685,673 | B2 | 2/2004 | Minezaki | |
| 7,041,081 | B2 | 5/2006 | Minezaki | |
| 2004/0019325 | A1 | 1/2004 | Shekalim | |
| 2004/0077998 | A1 * | 4/2004 | Morris | A61M 5/14 604/93.01 |
| 2004/0082912 | A1 | 4/2004 | Minezaki | |

FOREIGN PATENT DOCUMENTS

| | | |
|---|---|---|
| JP | 3274159 | 4/2002 |
| KR | 10-1998-0075314 | 11/1998 |
| WO | WO 2007/115039 | 10/2007 |
| WO | WO 2010-138170 | 12/2010 |

* cited by examiner

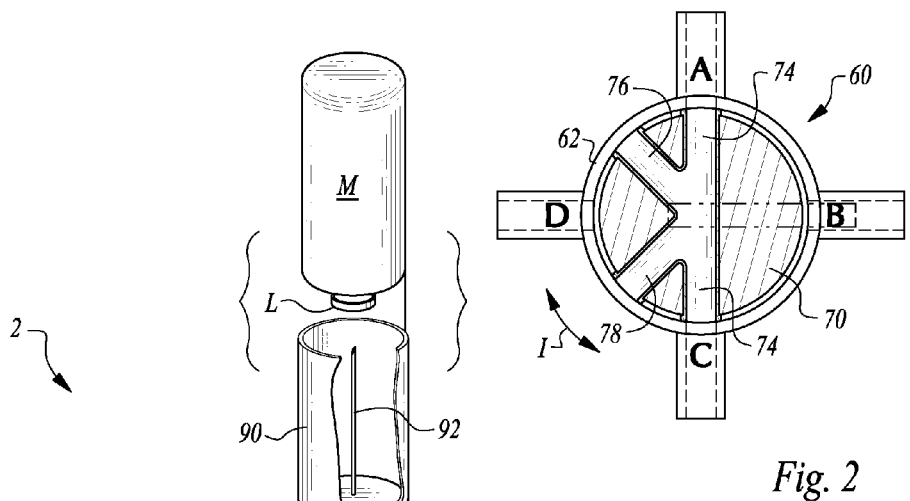
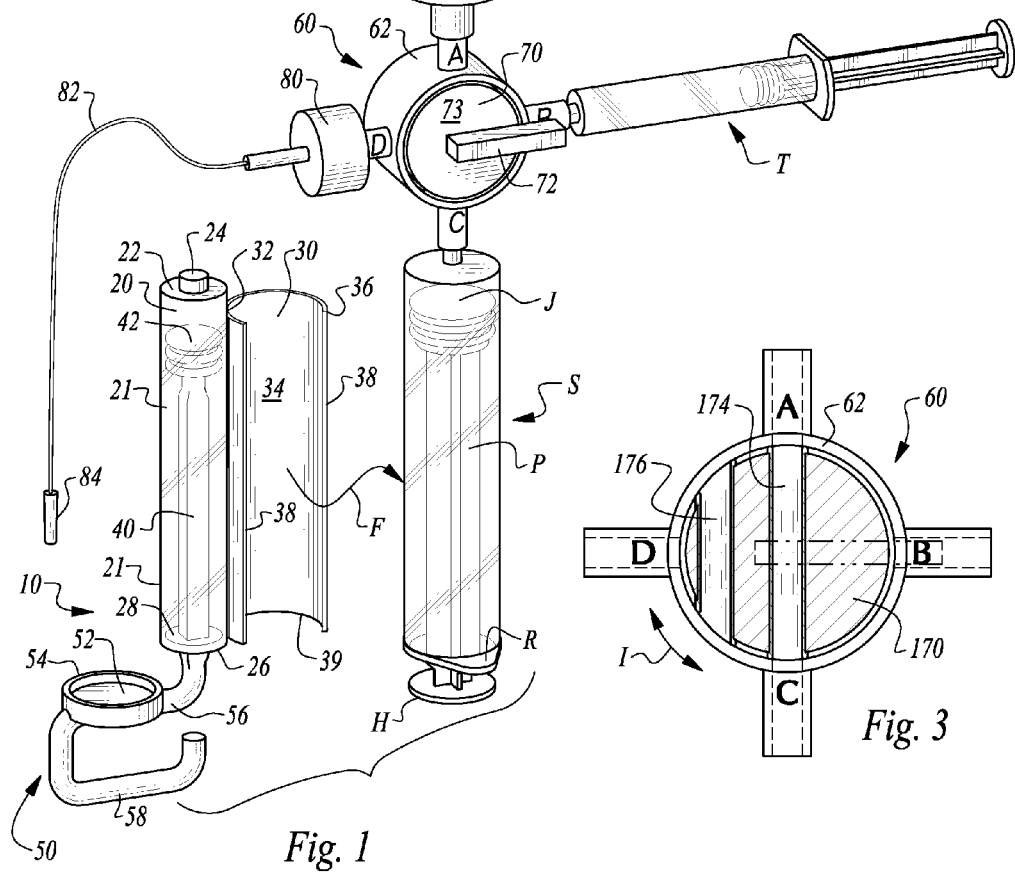
Fig. 2
Fig. 3
Fig. 1

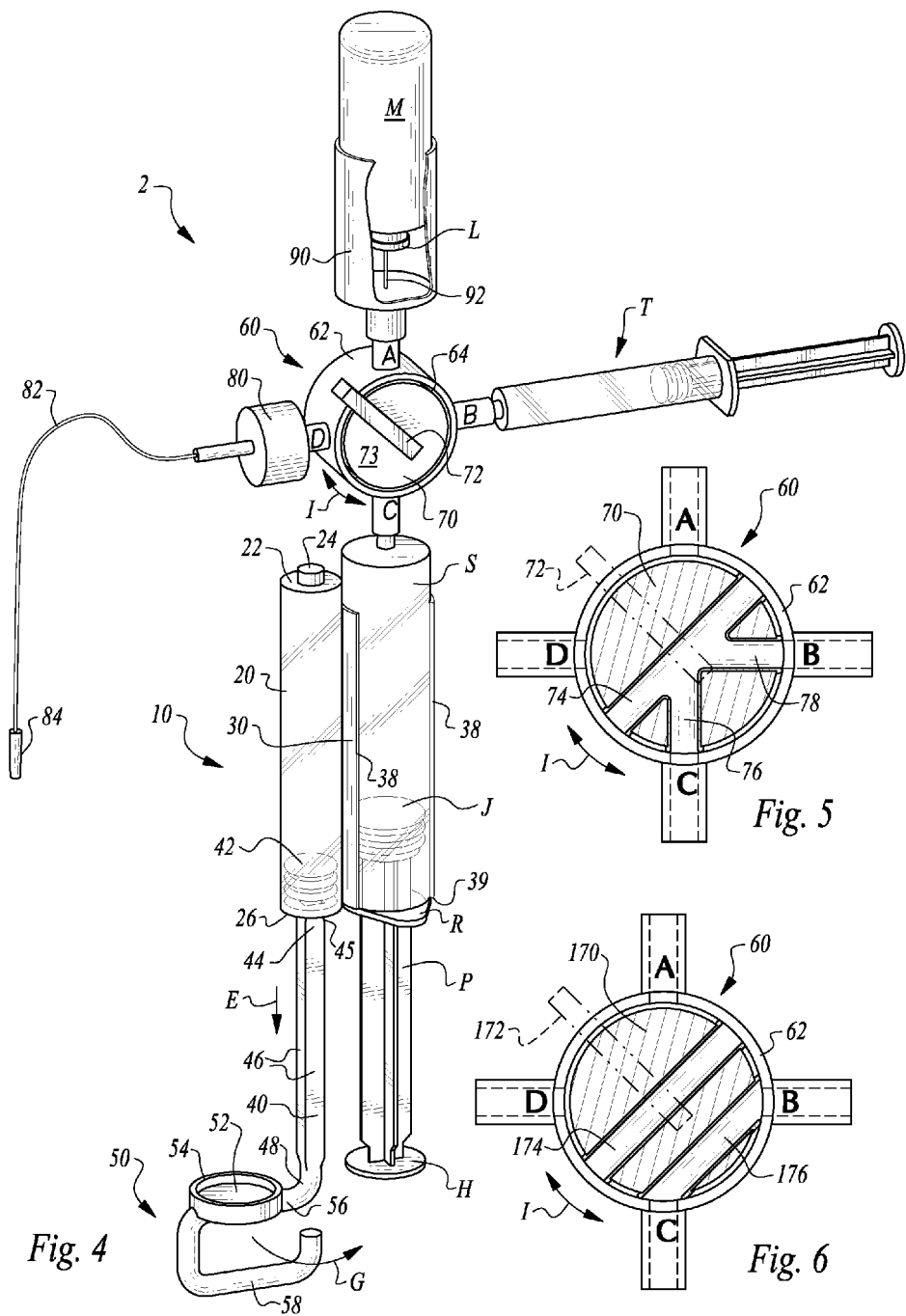

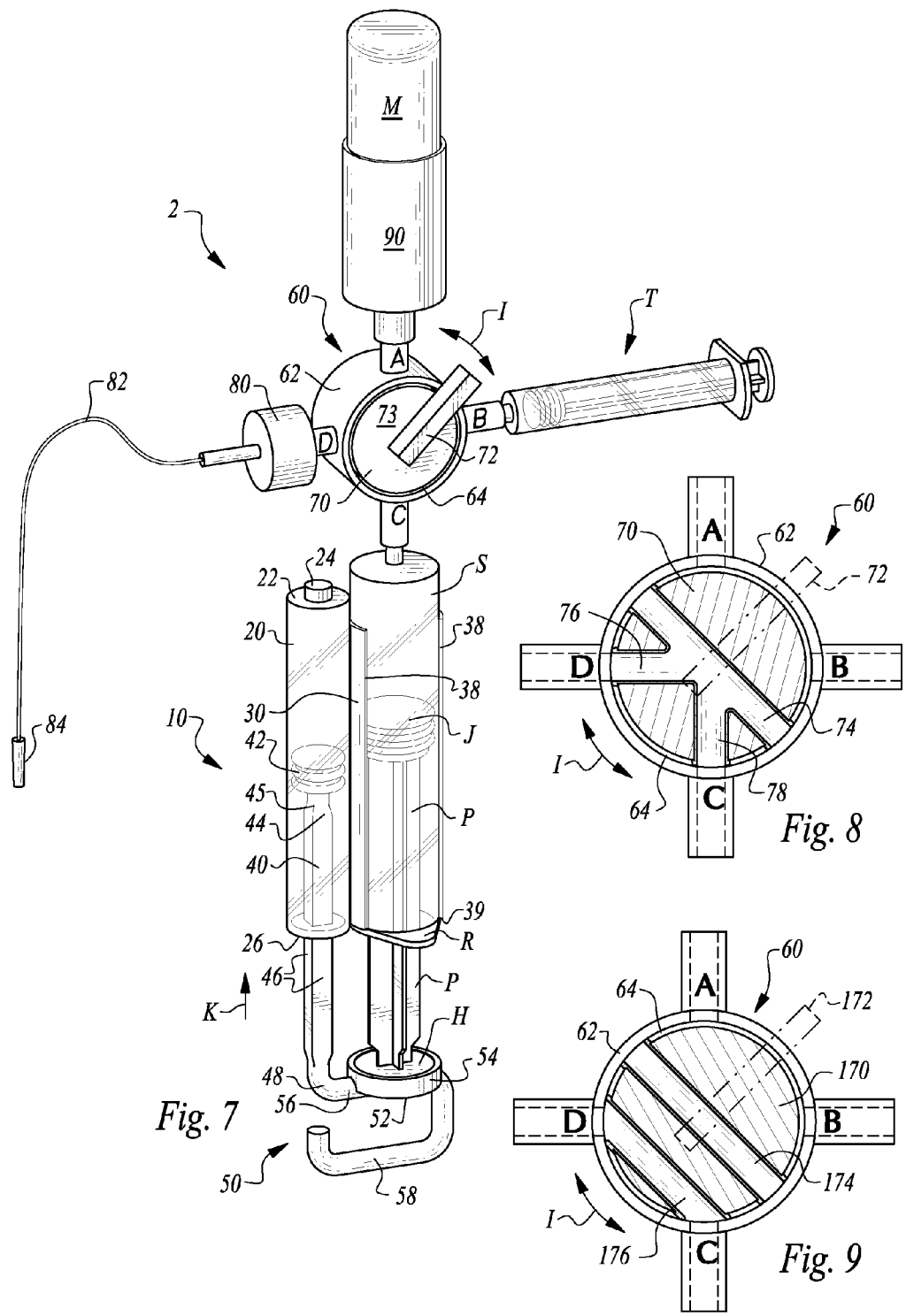

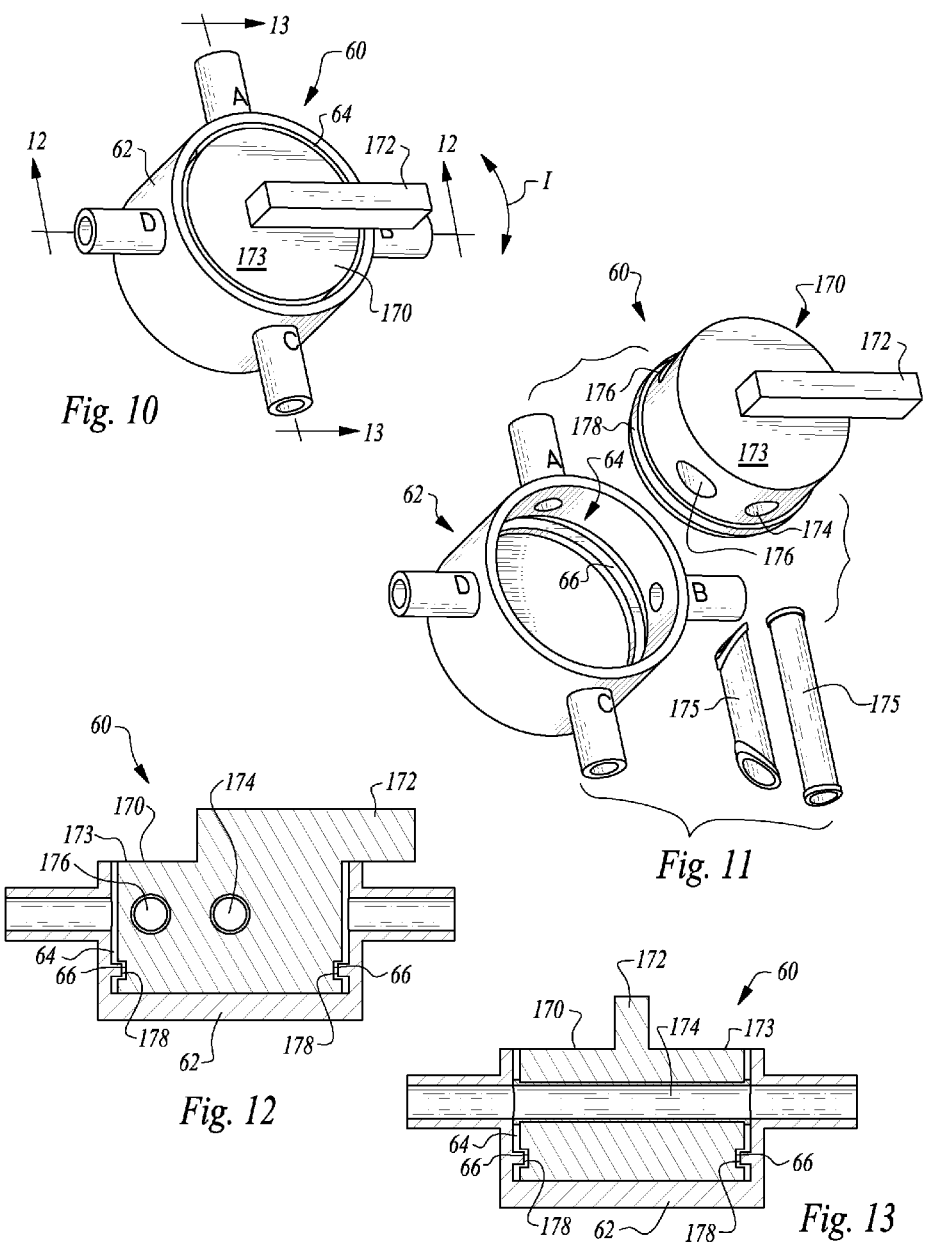

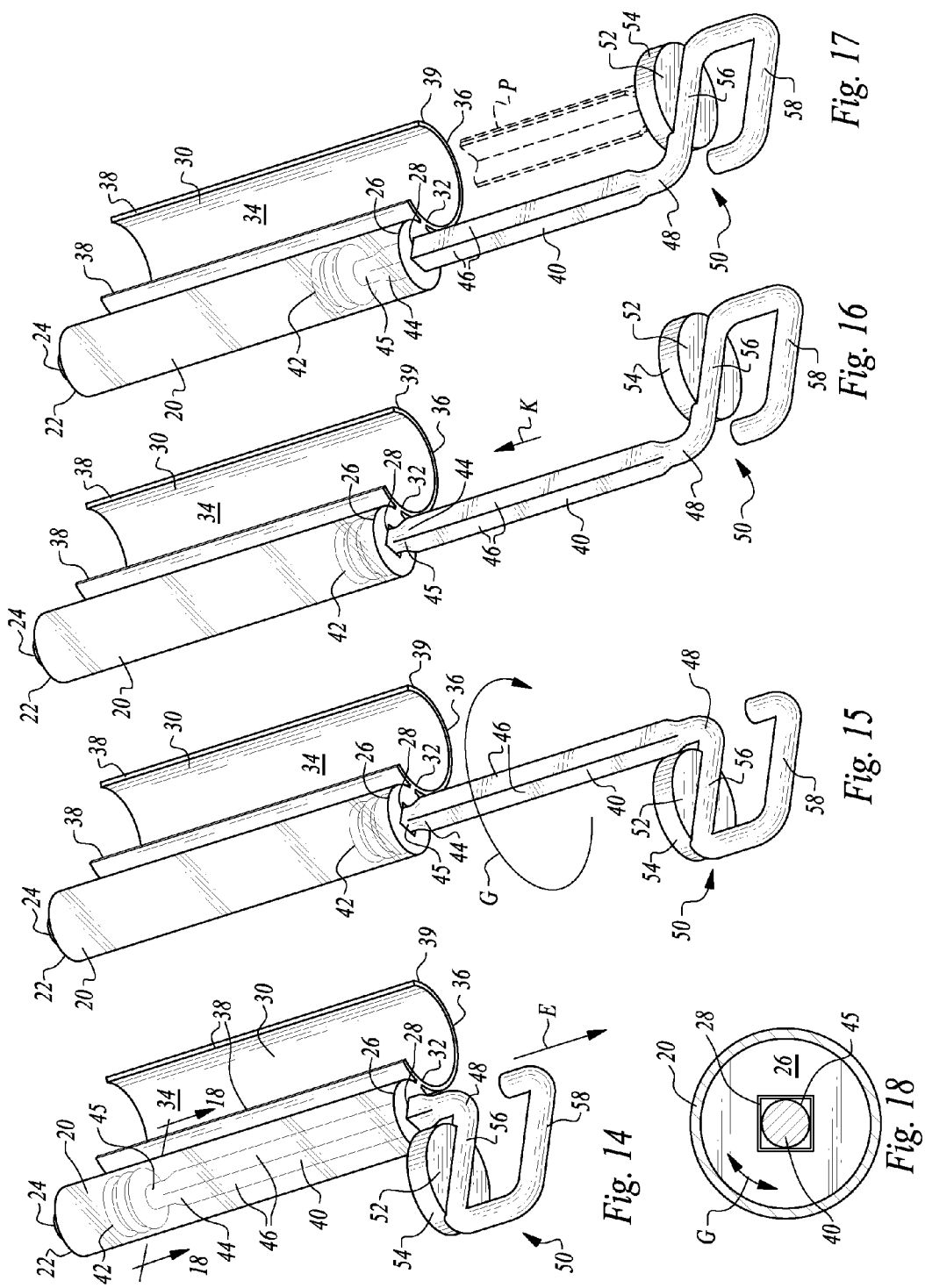

COMPACT NON-ELECTRIC MEDICAMENT INFUSER

CROSS-REFERENCE TO RELATED APPLICATIONS

This application claims priority from International Patent Application No. PCT/US2012/000550 filed on Nov. 8, 2012.

FIELD OF THE INVENTION

The following invention relates to infusion equipment for delivering medicament (medication or other medical preparations) into the bloodstream or other locations within the body of a patient or animal. More particularly, this invention relates to infusion devices which work with a standard medical syringe to deliver medicament from the syringe over a desired period of time and in a manner which does not require electronics or coupling to an external power source for proper function.

BACKGROUND OF THE INVENTION

Many medicaments require infusion into a patient or animal over an extended period of time, rather than in a single immediate dose. Infusion systems are known in the art to allow such medicaments to be so infused in a controlled fashion over a period of time. Such infusion systems generally include an intravenous access point where a medical professional has already placed an "IV" into the patient with medical tubing coupled to a needle penetrating the skin and typically into a vein of the patient. Additionally, such infusion systems include some form of reservoir for containing the medicament to be delivered and some form of infusion device for causing the medicament to move along the infusion tubing and through the IV into the patient.

In perhaps a simplest infusion system, gravity provides the force required by merely placing the reservoir at a height elevated relative to the IV intravenous access point. Gravity fed infusion systems have limitations in that the amount of force cannot be readily changed, other than through the imprecise method of increasing the elevation of the supply reservoir.

In other infusion systems an infusion pump is provided which applies a force on the fluid in the reservoir or along the infusion tubing to cause the fluid to move into the patient at the intravenous access site. One form of infusion pump acts on a medicament containing vessel in the form of a syringe by merely pushing on the plunger of the syringe at its proximal terminal end to deliver a medical preparation from the syringe. Such infusion pumps generally include some form of complicated electromechanical linear displacement transducer which converts an electric signal from a controller into mechanical motion in the form of linear motion acting on the plunger, to cause dispensing of the medical preparation from the syringe reservoir. The linear displacement transducer can be in the form of a solenoid type device or in the form of some form of motor, such as a stepper motor acting upon a rack and pinion type gear to convert rotating motion into linear motion. Other linear displacement transducers can also be utilized within such infusion pumps to convert the electric control signal into mechanical motion.

These electronic infusion pumps have the benefit of being able to utilize electrically driven displays and commonly available buttons and dials for thorough control of infusion rates and volumes, but also have significant deficiencies including a reliance on their internal mechanisms and a continuous source of electricity. If the power supplied from the AC plug or the DC battery is discontinued, full or partial failure of the pump may occur, causing incomplete or inaccurate medication delivery. The pump may also fail with respect to its electronic or mechanical parts within. These sorts of failures often lead to medication errors causing significant patient morbidity and mortality. These complex, expensive pumps increase the cost of delivering medical care, are cumbersome to use, require troubleshooting and frequent service. In addition, some magnetic or electric medical equipment can be interfered with by other equipment containing metal or generating electric signals, presenting a need for non-electric and/or nonmetallic infusion devices. These electronic devices cannot be used near an MRI scanner, but the patients often require ongoing infusion of their medicines, therefore a nonmagnetic/non-electronic device would be desirable.

Accordingly, a need exists for a simple but reliable medicament infusion system which utilizes an infusion device that does not require an electric power supply, can function reliably, and has low cost.

The prior art patents to Yamada (U.S. Pat. No. 5,807,337) and Mitchell (U.S. Pat. No. 5,024,664) demonstrate vacuum powered infusion devices with several limitations and have never attained significant clinical use. These devices connect the drive section to the syringe/load chamber section, which does not allow for independent operation of the two sections. This deficiency does not allow one to use the syringe section to self load by aspiration, nor does it allow one to readily discontinue and/or restart infusion by disengaging or reengaging the drive section from the medicament containing (syringe-like) section. These devices require the user to obtain and load a separate syringe so they can forcefully inject the desired medicament into the load chamber against the vacuum force of the connected drive section through a loading port which is occasionally separate from the infusion port. This obviously requires one to measure and load a separate syringe containing the medicament, attach it to the load chamber of the infusion device and apply an undue amount of finger pressure to force the medicament from the separate syringe into the load chamber as the user must overcome the vacuum force during this filling procedure. These additional steps, such as loading one syringe first to inject medicament into another, greatly increases the chance of medication error. Another limitation with these infusers is the lack of a guide or stabilizer to assure linear translation of the plungers during infusion. If the Yamada or Mitchell device plungers were significantly extended as with a significantly "full" device, there would be degree of rotation, flex and increased "play" in the apparatus which would allow increased friction and unreliable or nonlinear infusion rates. Another limitation of the Yamada and Mitchell devices is the difficulty faced with a loss of vacuum. The Mitchell device does not have a port to reestablish a vacuum should it be lost and the Yamada device has a "plug formed of a resilient material such as rubber" which requires removal in the event the vacuum needs to be replenished or if one wishes to alter the degree of vacuum force. Manipulation of a rubber plug is cumbersome and time consuming. Another limitation of these devices is the lack of a handle to independently operate the drive section. This deficiency is severely limiting and clearly demonstrates these devices are meant to be loaded with medicament only through the use of the second syringe as mentioned above, thereby extending the load chamber and drive section together and not allowing for independent operation of either section. This deficiency yields an inability to rapidly discontinue, start, or restart medicament infusion and maintains the load chamber in an always pressurized state making any attempt at placing medicament into the device cumbersome.

A prior art patent to Minezaki (U.S. Pat. No. 7,041,081) demonstrates a vacuum powered infusion device with many limitations. The device rigidly connects the drive section to the syringe/load chamber section, which does not allow for independent operation of the two sections. These deficiencies do not allow one to use the syringe section to self load by aspiration, nor does it allow one to readily discontinue and/or restart infusion by disengaging or reengaging the drive section from the medicament containing section. The device requires the vacuum section to be cocked back and locked with a "stopper capable of locking the piston at the rear end of the vacuum pump barrel against atmospheric pressure," before the two sections are placed together, and requires the vacuum barrel to be placed "in a state in which the front end of the vacuum pump barrel of said first structure extends further forward than the front end of the liquid syringe." One preferred embodiment of this device includes a version with the need for two medicament reservoirs connected together which is complicated and expensive. A second preferred embodiment demonstrates a rigidly aligned coaxial version which does not offer the independent functions required as the two sections are again rigidly connected. Other prior art patents Minezaki (U.S. Pat. No. 6,685,673) and Hiejima (U.S. Pat. No. 6,139,530) also demonstrate coaxial mechanisms with similar limitations.

Accordingly, a need still remains for a simple but effective non-electric self powered infusion device and system for delivering medicament into a patient in a reliable controlled fashion.

SUMMARY OF THE INVENTION

With this invention a medication infuser is provided which is compact and not reliant on electric power, and which includes an infusion device as part of an overall infusion assembly which is of a simple nature and yet can reliably deliver medicament from a reservoir into the patient. The overall assembly includes an infusion device coupled lateral to a standard syringe. This coupled arrangement may be reversible where the syringe is removable or may include a unification of the syringe and infuser through bonding or molding. A preferred embodiment of the infusion device includes a chamber within an outer body coupleable to the medicament containing syringe, such as by way of a clamp. A reciprocating arm is provided which is aligned with a long axis of the chamber to move into and out of the chamber. This arm has a sliding sealed piston on one end and a driver with a handle at the other end. This sliding sealed piston prevents air from passing around the arm and into a space between the sliding sealed piston and an interior of the chamber. This space can thus reliably hold a vacuum therein to provide a resistance force tending to cause the arm to move into the chamber (incursion) unless sufficient opposing forces are applied. Such opposing forces would include activating the infusion device by pulling out on the handle (excursion) or resistance by the syringe plunger as it pushes fluid out during infusion.

The reciprocating arm is configured so that it can rotate in a preferred form of this invention. Such rotation allows the driver to engage a plunger of the medicament containing syringe in some orientations and be free of interference with the plunger of the medical preparation containing syringe in other orientations. During infusion, the arm is generally prevented from rotation or lateral motion so that it provides stable linear force transfer for infusion to the plunger of the medication containing syringe.

The infusion assembly also preferably includes a valve, such as in the form of a stopcock to which the medicament containing syringe is coupled through a first port. A second port leads to an intravenous access port or other interface with a patient, typically through a flow rate regulator. The stopcock valve can have other ports, such as a port through which medicament is initially supplied for loading of the medicament containing syringe. This medicament can be supplied through a single port or through multiple ports, such as through a medical vial adapter interface or through a secondary syringe, or through both, such as when the medication within the vial needs to be measured or mixed with a diluent material such as saline before being loaded into the medicament delivery syringe.

This stopcock is preferably configured so that it is easily manipulated between different positions to cause flow of the medicament or constituents thereof in different directions depending on whether the medicament delivery syringe is being loaded or unloaded and whether the medicament is being supplied from a vial or syringe, or is ready to be delivered to the patient. All parts of the infusion assembly including the infusion device operate without requiring electric power or other electric systems. Furthermore, such systems do not require a particular orientation relative to gravity for effective operation.

OBJECTS OF THE INVENTION

Accordingly, a primary object of the present invention is to provides an infusion device which is non-electric.

Another object of the present invention is to provide a medicament infusion device which can operate reliably and which is durable for reliable and long-term use.

Another object of the present invention is to provide a medicament infuser which is compact in form and easy to set up and operate.

Another object of the present invention is to provide a medicament infuser which can be flexibly operated in a variety of different ways, including receiving medical preparations from a variety of different initial sources and being readily activated and deactivated for flexible performance in accordance with the desires of medical professionals.

Another object of the present invention is to provide a low cost medicament infusion system.

Another object of the present invention is to provide a medicament infusion system where at least part of the system is disposable.

Another object of the present invention is to provide a medicament infusion system with a lower rate of medication errors.

Another object of the present invention is to provide a medicament infusion assembly which can be utilized to accept medicament from a variety of different initial sources, including liquid and powdered preparations, into a reservoir from which it can be infused into a patient.

Another object of the present invention is to provide an infusion assembly which does not require a particular orientation relative to gravity for proper function.

Another object of the present invention is to provide a medicament infusion system which is compatible with MRI scanners.

Another object of the present invention is to provide an infusion device which can infuse a medicament from a standard syringe.

Another object of the present invention is to provide an infusion device which can be integrated into a standard type disposable intravenous administration set.

Another object of the present invention is to provide a medicament infuser that may be easily attached to the patient.

Other further objects of the present invention will become apparent from a careful reading of the included drawing figures, the claims and detailed description of the invention.

BRIEF DESCRIPTION OF THE DRAWINGS

FIG. 1 is a perspective view of the infusion assembly of this invention and showing the infusion device of this invention ready to be attached to a medicament containing syringe. Also, the stopcock valve, medication bottle and associated interface, second syringe coupling to the stopcock valve and patient interface are shown.

FIGS. 2 and 3 are top plan full sectional views of the stopcock valve of FIG. 1, showing two different alternative embodiments for orientation of internal embedded fluid flow pathways within a manifold hub of the stopcock valve to provide flow as desired within the infusion assembly.

FIG. 4 is a perspective view similar to FIG. 1, but with the infusion device having been clamped onto the syringe and with the syringe shown loaded with the medicament and with the infusion device arm and driver ready to be rotated into position to drive the plunger of the syringe and deliver the medicament through the infusion assembly into the patient.

FIGS. 5 and 6 are top plan full section views similar to that which is shown in FIGS. 2 and 3, but for different orientations for the stopcock valve that correspond with FIG. 4.

FIG. 7 is a perspective view similar to that which is shown in FIGS. 1 and 4, but after the infusion device arm and driver has been rotated into position to act on the plunger of the syringe, and shown in the process of moving the piston to deliver medicament into the patient through the infusion assembly.

FIGS. 8 and 9 are top plan full sectional views similar to that which is shown in FIGS. 2, 3, 5 and 6 but for different orientations for the manifold hub of the stopcock valve.

FIG. 10 is a perspective view of the stopcock valve and associated manifold hub of this invention, particularly showing an alternative manifold hub according to an alternative embodiment of this invention.

FIG. 11 is an exploded parts view of that which is shown in FIG. 10.

FIG. 12 is a full sectional view of that which is shown in FIG. 10, taken along lines 12-12 of FIG. 10.

FIG. 13 is a full sectional view of the stopcock valve of FIG. 10, taken along lines 13-13 of FIG. 10.

FIGS. 14-17 are perspective views of the infusion device of this invention showing the various stages in the operation of the infusion device of this invention.

FIG. 18 is a full sectional view taken perpendicular to a long axis of the infusion device, and particularly showing how the arm of the infusion device has portions thereof which can rotate freely relative to a faceted alignment guide opposite a distal end of the infusion device, and other positions where such rotation of the arm relative to the alignment guide is prevented.

DESCRIPTION OF THE PREFERRED EMBODIMENT

Figure 19:
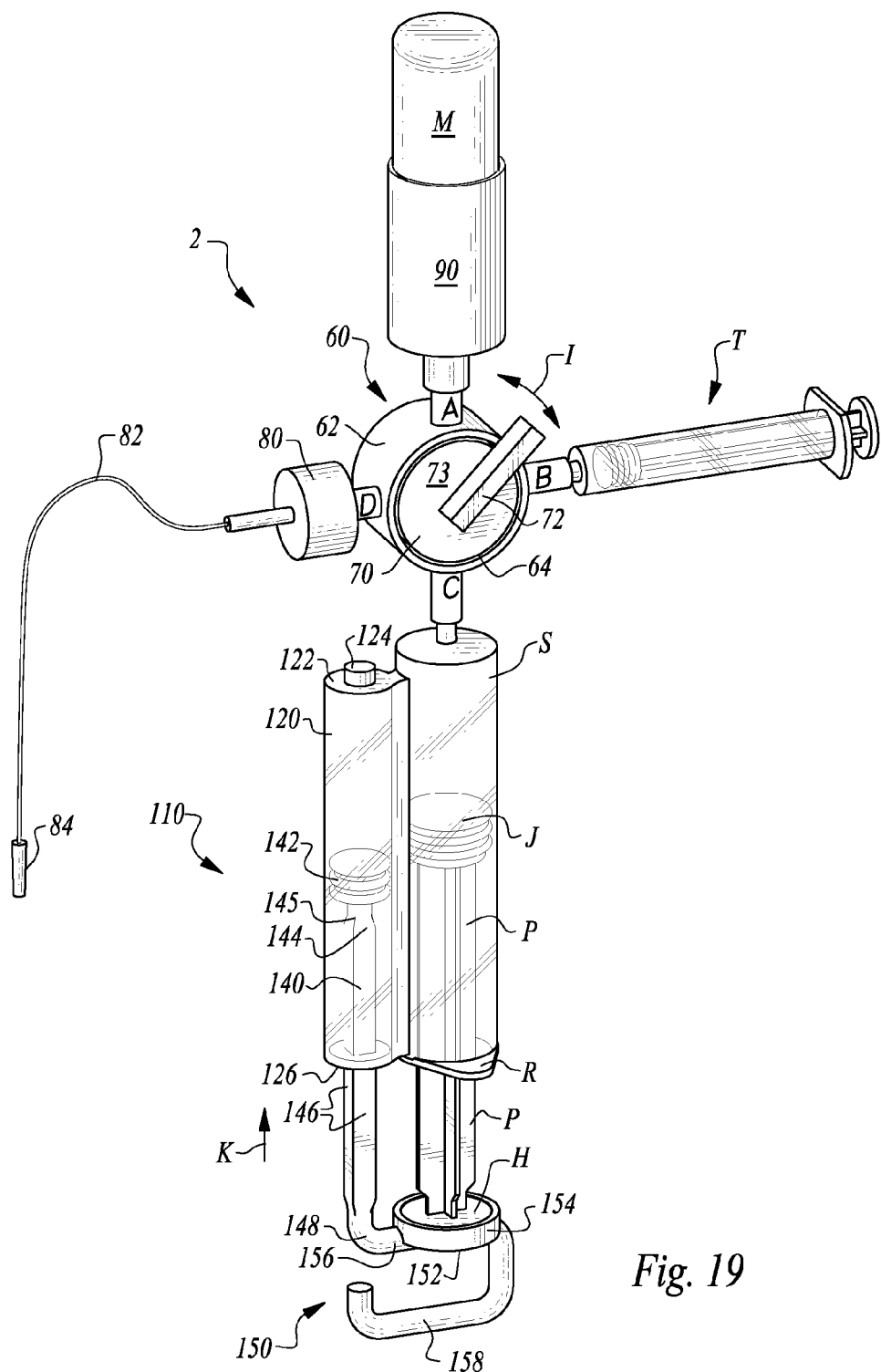
FIG. 19 is a perspective view similar to FIGS. 1 and 7, but with the infusion section and the syringe section molded or bonded together as a single unit.

Referring to the drawings, wherein like reference numerals represent like parts throughout the various drawing figures, reference numeral 10 is directed to an infusion device for use with a syringe S, such as within an overall infusion assembly 2 for delivery of medicament over time from the syringe S into a patient or animal. The infusion device 10 utilizes a vacuum or another resistance based force to energize and "activate" the arm 40 and driver 50. The arm 40 and driver 50 together are known as the force applicator and when activated, may act upon a plunger P of the syringe S so that a piston J within the syringe S moves to drive the medicament out of the syringe S and to the patient.

In essence, and with particular reference to FIG. 1, basic details of this invention are described, according to a preferred embodiment. The infusion assembly 2 in this preferred embodiment includes the infusion device 10 removably coupleable (along arrow F) to the syringe S. The syringe S is coupled to a stopcock valve 60 which has separate ports which act as inlets or outlets into or out of other portions of the infusion assembly 2. These ports A, B, C, D can lead to a second syringe T, a vial adapter 90 adapted to receive and assist in removal of a medicament from a medication bottle M, and a patient interface generally in the form of a regulator 80, a tube 82 and a connector 84. The regulator 80 may be integrated into the stopcock valve 60, the tube 82, or the connector 84, or may simply be accomplished by having small bore tubing 82 of appropriate diameter and length to act as a flow resistance regulator itself. The stopcock valve 60 includes a housing 62 which supports a manifold hub 70 therein. By rotation of the manifold hub 70, different ports A, B, C, D within the stopcock valve 60 are brought into fluid communication with each other for passage of fluid between the aligned ports and equipment coupled to these ports.

In the most preferred embodiment the infusion device 10 includes a body 21 around a chamber 20 in which a vacuum can be drawn. This vacuum chamber 20 can be replaced with a spring, gas cylinder or other resistance force based energizing means. A clamp 30 is coupled to the body 21 in this embodiment which allows the infusion device 10 to be snapped onto the syringe S, or the syringe S to be snapped into the infusion device 10 (along arrow F). A reciprocating arm 40 translates into and out of the chamber 20 with a sliding sealed piston 42 on an innermost (distal) end of the arm 40 and a driver 50 on the proximal end of the arm 40 opposite the sliding seal 42. The driver 50 is adapted to engage the proximal terminus H of a plunger P of the syringe S to cause the plunger P to move within the syringe S and cause medicament within the syringe S to be delivered therefrom. The arm 40 is rotatable to bring the driver 50 into and out of alignment with the proximal terminus H of the plunger P of the syringe S, for selective engagement and disengagement of the infusion device 10 by rotation of the arm 40 relative to the chamber 20.

More specifically, and with continuing reference to FIG. 1, as well as FIGS. 4 and 7, standard details of the infusion assembly 2 which are generally available alone in the prior art are described to provide proper context for understanding of unique details of the infusion assembly 2 of this invention.

The syringe S is most preferably a standard syringe having a generally cylindrical hollow body forming a cylinder and with a plunger P translating into and out of this cylinder of the syringe S. The cylinder includes a fluid conveyance port typically at a distal end and an opening surrounded by a radially extending ledge R at a proximal end which allows the plunger P to pass into and out of the interior of the cylinder. The plunger P includes a proximal terminus H on a proximal end thereof and a piston J on an end of the plunger P opposite the proximal terminus H. The piston J includes seals thereon so that fluid cannot move around the piston J as the piston J moves within the syringe S cylinder. The fluid conveyance port of the syringe S is adapted to be coupled to one of the ports of the stopcock valve 60. In this exemplary embodiment, the syringe S is shown with the fluid conveyance port coupled to port C of the stopcock valve 60. Such a connection can merely be through a "luer" type fitting or some other type of coupling which is preferably a coupling which can be removably attached.

Because this syringe is preferably of a standard type, it would typically have graduation lines on a side of the body and associated indicia representative of volumetric capacity of the syringe S with the piston J at various different positions within the syringe S. With the syringe S in the form of a standard syringe in this preferred embodiment, the syringe S can be used in a variety of different ways known in the art either before or after attachment to the stopcock valve 60 (e.g. by utilizing any known technique for loading a syringe S before attachment to the stopcock valve 60 and utilization with the infusion assembly 2) or for loading of the syringe S in standard ways through the stopcock valve 60, or for manipulation of the syringe S manually by a user pushing on the plunger P of the syringe S when such manipulation of the syringe S is desired by a medical professional.

In addition to the syringe S, a second syringe T can be coupled to one of the ports. In this embodiment, such a second syringe T is shown attached to port B of the stopcock valve 60. The second syringe T can act as a medicament container, a measuring device or a mixing device, such as for accurately measuring a dose of medication or mixing a saline solution with a medication to properly measure, mix or dilute a medication contained in syringe T (or syringe S) or in a medication vial attached to another port before transferring the medication into the syringe S for delivery through the infusion assembly 2 of this invention. This capability would give the medical professional the ability to dilute a powdered (or liquid) medication attached at another port while in place, then dilute it, mix it, measure it, and transfer it to the syringe S for infusion. The second syringe T can also be utilized for holding a second volume of like or different medication which could either be co-infused along with a first medical preparation within the syringe S, or to be utilized on an itinerant basis at the direction of the medical professional. The second syringe T preferably interfaces with port B the same way that the syringe S interfaces with port C. Such syringes S, T and other components of the infusion assembly 2 can be coupled to any one of the ports A, B, C, D without any particular requirement that any particular component of the assembly 2 be coupled to any particular port A, B, C, D.

A medication bottle or vial M is known in the prior art which contains a medication and with a septum L often at an interface on the medication vial through which a needle can pass to draw a medical preparation out of the vial M. In this preferred embodiment, the infusion assembly 2 includes a vial adapter 90 with associated needle 92 extending axially therein. The vial adapter 90 and needle 92 are preferably coupled to one of the ports (port A in FIGS. 1, 4 and 7) of the stopcock valve 60. Such a coupling can be similar to the coupling for attachment of the second syringe T or syringe S to the stopcock valve 60 through other ports B, C. Thus, a medication vial M can be inserted into the vial adapter 90 and a needle 92 can pierce the septum L of the medication vial M. The medical preparation (medicament) can then be drawn out of the medication vial M through the needle 92 and into the stopcock valve 60 for delivery to any of the other portions of the infusion assembly 2 coupled to the stopcock valve 60.

The vial adapter 90 is available as prior art and typically somewhat cylindrical and open at one end. It is typically long enough to prevent or discourage fingers of a medical professional from bumping into the tip of the needle 92. Also, the vial adapter 90 helps to align the medication bottle M with the needle 92 so that the needle 92 can reliably hit the septum L and penetrate the septum L. The vial adapter 90 can have different diameters to accommodate different medication bottle sizes or could otherwise be configured to more flexibly accommodate different medication vials M of different sizes while still providing some degree of protection from inadvertent contact with the needle 92.

With these various components of the infusion assembly 2 which are known in the prior art being able to interface with the stopcock valve 60, the infusion assembly 2 is provided with equipment that is familiar to medical professionals so that the operation of the infusion assembly 2 is simple and intuitive for the medical professional. Furthermore, flexibility in the interconnection of various medical components is to some extent facilitated by the interchangeability of the ports in the stopcock valve 60 and the general configuration of the infusion assembly 2 which allows for flexible arrangement of different medical equipment into the infusion assembly 2.

The fourth port D of the stopcock valve 60 typically is coupled to some form of patient interface, such as through a tubing 82, a regulator 80 and a connector 84. The regulator 80 may be a discreet part or may be integrated into the stopcock 60, tubing 82 or connector 84. The regulator 80 can act as a fixed or adjustable control for flow rates into the patient. If adjustable, it would typically have dials, buttons or some other manipulatable interface and perhaps a display indicating its current setting. The tubing 82 is preferably flexible and elongate so that the infusion assembly 2 is not required to be located too close to the patient. The connector 84 would typically be in the form of a male luer lock adapter, a simple intravenous access needle, or any other form of prior art connector able to connect into the patient's intravenous, intraarterial, intraosseous, or other body lumen system as desired by the medical professional.

With continuing reference to FIGS. 1, 4 and 7 primarily, details of the infusion device 10 of the infusion assembly 2 are described. While the infusion device 10 is described in conjunction with the entire infusion assembly 2, it is conceivable that the infusion device 10 could merely be used with a single syringe S directly coupled to some form of patient interface without the stopcock valve 60. Furthermore, the infusion device 10 could conceivably be utilized for distribution of any fluid from the syringe S even in a non-medical environment, such as in a laboratory or industrial setting for timed release of a fluid. Furthermore, the infusion device 10 might be utilized on a syringe S for delivery of a fluid within some form of manufacturing process where delivery of a fluid at a somewhat regular rate over time is required, and where it is desired that the infusion device 10 exhibit the simplicity and non-electric nature of the infusion device 10 of this invention.

The infusion device 10 in this preferred embodiment utilizes an energy storage and resistance force application principle (resistance force energizer) that is generally associated with a vacuum within a chamber 20 of the infusion device 10. It is known that within the atmosphere and in other environments where a fluid pressure is present, that if a vacuum is formed in a particular location that forces are exerted to tend to close up this vacuum space. Essentially, in our atmosphere the air within the atmosphere pushes on all walls of the vacuum space to try to close up this vacuum space. Such a force is utilized by the infusion device 10 in this preferred embodiment to provide the force required to act on the syringe S to cause delivery of medicament into the stopcock valve 60 for operation of the infusion assembly 2 of this invention.

The preferred embodiment infusion device 10 is generally configured similarly to a standard medical syringe. The body 21 and chamber 20 are thus generally cylindrical in form and elongate along a central axis. One end of the chamber 20 is closed defining a distal end 22. This distal end 22 preferably includes a port with a form of closure 24 such as a cap or an open/close valve. Such a distal port and closure 24 are useful in that they allow installation of an arm 40 with an associated sliding sealed piston 42 into the chamber 20 and evacuation of any air or other fluids within the chamber 20 during such installation or such as to restore the vacuum state within the chamber 20 should it ever be lost for any reason (such as removal of the arm 40 or extension of the sliding sealed piston 42 too far out of the chamber 20, causing loss of the vacuum state within the chamber 20).

A ported base 26 is provided on the proximal aspect of the infusion device body 21 opposite the distal end 22 acts as a proximal end of the chamber 20 which is generally perpendicular to the long axis of the body and does retain the sealed piston 42, but is not a fluid tight barrier in the vacuum powered version because atmospheric pressure must reach the proximal side of the sealed piston to impart its force on the piston (as the vacuum chamber exists on the distal side of the piston). In a preferred embodiment, this ported base 26 includes a faceted alignment guide 28 which provides an opening through which the arm 40 can reciprocate.

In a most preferred embodiment of this invention this faceted alignment guide 28 has facets thereon which only allow the arm 40 to translate therethrough when the arm 40, having matching or corresponding facets 46, is properly aligned for passage through the faceted alignment guide 28. In other orientations of the arm 40, the faceted alignment guide 28 can interact with facets 46 on the arm 40 to prevent arm 40 translation through the faceted alignment guide 28 of the ported base 26.

The chamber 20 may be sized larger, smaller or similarly to the syringe S to provide various different degrees of force application and various different associated infusion rates for the infusion device 10. Typically, the chamber 20 is formed of plastic materials similar to those from which syringes are typically formed. The contour of the chamber 20 is preferably formed to be amenable to manufacture by injection molding or similar low cost manufacturing processes so that the infusion device 10 can be manufactured in a precision manner at low cost to desirably provide both robust and low cost performance to the user.

A clamp 30 is included with the infusion device 10 for attachment of the infusion device 10 to the syringe S. In this preferred embodiment, the clamp 30 is coupled directly to the body 21 of the infusion device 10. The clamp 30 is elongate in form, and typically having a length approximating the syringe S length. The clamp 30 is attached to the body 21 through a joint 32 which is preferably fixed so that the clamp 30 does not move relative to the body 21 and may be molded with the body 21 as a unit.

The preferred clamp 30 is a semi-cylinder of hollow nature so that it has an inside wall 34 forming a portion of a cylinder and an outside wall 36 forming a portion of a cylinder (although shapes other than a cylinder could be utilized as an effective clamp). Edges 38 define ends of these walls 34, 36. Preferably, the clamp 30 is slightly more than half of a full cylinder. Thus, the edges 36 extend slightly toward each other and are closer to each other than a diameter of the cylindrically shaped clamp 30. The clamp 30 is preferably formed of sufficiently resilient material that the edges 38 can be flexed away from each other slightly. This material is also preferably sufficiently elastic that the clamp 30 will apply a clamping force tending to cause the clamp 30 to return at least partially back toward an original state and continue to maintain an inwardly directed clamping force to help the clamp 30 securely attach to the syringe S.

Furthermore, the clamp 30 has a proximal end 39 which is preferably substantially planar and perpendicular to a long axis of the clamp 30 and chamber 20. This proximal end 39 is configured to abut against the ledge R at the proximal end of the syringe S. One such ledge R is shown in FIGS. 1, 4 and 7 on a front side of the infusion assembly 2. However, such a ledge R typically extends at two locations opposing each other on opposite sides of the syringe S, with a rearward ledge hidden behind the body of this syringe S, but having a similar form to that of the ledge R on the front side that is shown in FIGS. 1, 4 and 7.

The distal aspect of At least one of these ledges R on the syringe S provides an abutment surface for the proximal end of the clamp 30 so as to prevent translation of the infusion device 10 proximal to the syringe S and although not shown in the figure, an additional abutment surface attached to the body 21 and abutting upon the proximal aspect of the ledge R could be added to reduce translation of the infusion device 10 distal to the syringe S. With such an interface against the ledge R, it is not strictly necessary that the clamp 30 grip the syringe S sufficiently strongly to prevent translation of the clamp 30 and body 21 of the infusion device 10 along a central axis of the infusion device relative to the syringe S. Rather, the clamp 30 need merely provide sufficient force to keep the infusion device 10 on the syringe S, with the interface between the proximal end 39 of the clamp 30 and the ledge R preventing axial translation between the syringe S and the infusion device 10.

Thus, the clamping force 30 that must be overcome to snap the clamp 30 onto the syringe S (along arrow F of FIG. 1) does not need to be so great that it can also act to hold the infusion device 10 without translation relative to the syringe S. Vacuum forces within the chamber 20 and acting on the arm 40 can be quite high, and hence forces tending to translate the infusion device 10 longitudinally relative to the syringe S can be quite high. Because the clamping force requires factoring in of friction between the clamp 30 and the syringe S, clamping forces of the clamp 30 would need to be exceptionally high to alone prevent translation of the infusion device 10 relative to the syringe S. By having the proximal end 39 of the clamp 30 abut the ledge R, clamping forces 30 can be kept at a relatively low level so that even a medical professional with limited strength can easily attach and detach the infusion device 10 onto and off of the syringe S.

With continuing reference to FIGS. 1, 4 and 7, details of the arm 40 and associated driver 50 of the infusion device 10 are described, according to this preferred embodiment. The arm 40 provides the preferred form of interconnection between a sliding sealed piston 42 which slides within the chamber 20 and a driver 50 which is a preferred form of interface with the plunger P of the syringe S. This arm 40 is preferably an elongate substantially rigid structure sized to reside within the chamber 20 and reciprocate (translate axially) within the chamber 20 along a central axis thereof.

The sliding sealed piston 42 is provided at a distal end of the arm 40. This sliding sealed piston 42 is similar to the piston J of the syringe S, and is configured to have a friction fit against interior walls of the chamber 20, and formed with a sufficiently rigid material so that a fluid-tight fit is provided between the sliding sealed piston 42 and walls of the chamber 20. Thus, as the arm 40 reciprocates into and out of the chamber 20, the sliding sealed piston 42 also moves within the chamber 20 and a volume of a vacuum space between the sliding sealed piston 42 and the distal end 22 within the chamber 20 is caused to increase and decrease in size.

A preferred embodiment of the infusion device includes the sliding sealed piston 42 coupled to a free end 44 of the arm 40 which extends most deeply into the chamber 20. This free end 44 preferably is configured with a neck 45 defining a portion of the arm 40 which has a slightly smaller cross-sectional diameter than other portions of the arm 40. This cross-sectional diameter is preferably also circular in form, but also could have other shapes and still function as the neck 45 provided that it is either smaller in size or closer to round than other portions of the arm 40.

The arm 40 extends proximally away from the free end 44, the neck 45 preferably transitions into series of facets 46 which provide the arm 40 with a cross-sectional shape which remains constant but which is faceted rather than circular in form. These facets 46 can take on a variety of different configurations including convex and concave angles. In a simplest form of the invention, four similarly sized facets are provided so that the arm 40 has a generally square cross-section.

This contour for the cross-sectional shape of the arm 40 is similar to that of the faceted alignment guide 28 of the chamber 20. Thus, the arm 40 can translate through the faceted alignment guide 28, but the arm 40 is prevented from rotating relative to the faceted alignment guide 28. However, when the neck 45 portion of the arm 40 is aligned with the faceted alignment guide 28, such rotational restriction is eliminated and the arm 40, sliding sealed piston 42, as well as the driver 50 can be rotated as a unit relative to the chamber 20, body 21 and clamp 30 (arrow G of FIGS. 4 and 15). When the arm 40 is moved so that it is not aligned with its neck 45 portion adjacent the faceted alignment guide 28, then the faceted portion 46 of the arm 40 will be mated with (and cooperating with) the faceted alignment guide 28. This will tend to keep the arm 40 highly stable and precisely aligned along a central axis of the chamber 20 so that the driver 50 will remain precisely aligned with the proximal terminus H of the plunger P of this syringe S, to provide the infusion device 10 as a very stable force applying means, acting on the syringe S for infusion therefrom (along arrow K of FIGS. 7 and 16). The force that the infusion device applies during incursion (translation inward), to the syringe proximal terminus, will be translated to actual work performed on the syringe plunger as the plunger moves inward causing infusion of medicament.

An end of the arm 40 opposite the free end 44 includes a bend 48 thereon which transitions into the driver 50. The driver 50 is an extension or transition of the arm 40 which includes a handle 58 and a thrust area 52, 54. The thrust area 52, 54 can interface with and thrust the proximal terminus H of the plunger P of the syringe S to cause infusion. In a preferred form of the invention, the driver 50 thrust area 52, 54 includes an engagement plate 52 and associated rim 54. The engagement plate 52 is generally planar and oriented perpendicular to the central axis of the chamber 20. This plate 52 preferably includes a cylindrical rim 54 extending distally from a perimeter of the plate 52. This rim 54 has a diameter slightly greater than the proximal terminus H of the plunger P of the syringe S, with the proximal terminus H typically being substantially round. Thus, when the proximal terminus H is adjacent the engagement plate 52, the rim 54 keeps the driver 50 aligned with the proximal terminus H to further assist in stabilizing the assembly of the infusion device 10 clamped to the syringe S. The rim 54 may not need to encompass the entire perimeter, but only a portion adequate to resist any movement of the proximal terminus H.

Figure 21:
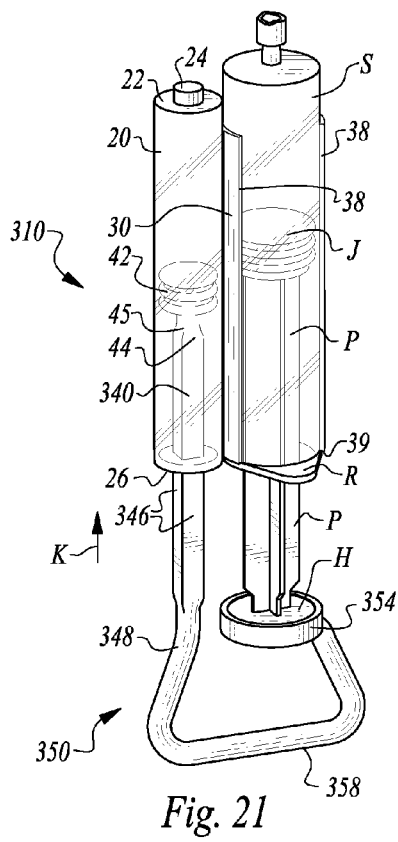
FIG. 21 is a perspective view similar to FIG. 7, but with the infusion driver's handle and thrust area oriented differently. Here the thrust area is positioned on the end of the driver's loop like handle, rather than that location shown in the other figures where it is positioned on the transverse member more near the first bend in the arm. The handle and driver's function is still essentially identical, but there is a "loop" rather than an open "hook" formed by the handle during infusion.

In FIGS. 1, 4, 7, 14, 15, 16, 17 and 18 a transverse member 56 extends from the bend 48 to a rear side of the plate 52 to interconnect the engagement plate 52 to the arm 40. This transverse member 56 preferably further bends to form a hook 58. Such a hook 58 can be utilized to suspend the entire infusion assembly 2, or at least the infusion device 10 and associated syringe S from an elevated support, if desired. In such an arrangement, the hook 58 would end up being the highest portion of the entire infusion assembly 2. This hook 58, also acts as a handle 58 which can be gripped by a user for pulling of the driver 50, arm 40 and sliding sealed piston 42 (along arrow E of FIGS. 4 and 14) against the resistance force (which in this embodiment includes the sliding sealed piston forced distally by the vacuum force) and for ease in rotation of the same structures (along arrow G of FIGS. 4 and 15). An embodiment shown in FIG. 21 demonstrates an alternate, but equivalently desirable design for the driver 50, handle 58 and thrust area 52, 54. In this embodiment the thrust area with the plate 52 and rim 54 are affixed to the distal most aspect of the handle 58, leaving a loop rather than a hook, when the infusion device 10 is actively engaged with the syringe S.

The driver 50 and arm 40 act as a preferred form of force application member (force applicator) to apply a linear force on the plunger P of the syringe S. In this embodiment, the driver 50 is caused to move by action of the arm 40 and the sliding sealed piston 42 being drawn into the vacuum between the sliding sealed piston 42 and the distal end 22 within the chamber 20. Provided that a pure vacuum exists between the sliding sealed piston 42 and the distal end 22 of the chamber 20, this force remains entirely constant and is proportionate to the atmospheric pressure outside of the vacuum chamber 20. Thus, a constant force is applied to the syringe S for discharge of medicament over the entire length of force applicator incursion.

In alternative embodiments, the vacuum chamber 20 can be replaced with some other form of energy storage and resistance force application principle (resistance force energizer). For instance, a tension spring could be placed between the driver 40 and a surface generally attached to the body 21. The spring would tend to hold the force applicator (arm 40 and driver 50) at its resting point (maximum incursion) until the user applies energy to produce excursion of the force applicator 40, 50, thereby stretching the tension spring and activating the infuser. The spring would then exert a force tending to return the force applicator 40, 50 back to its resting point, thereby inducing forced incursion (inward movement) of the driver 50 which would perform useful work on the syringe plunger P. Simultaneously, the driver 50 could supply this force to the plunger P of the syringe S.

As another alternative, the infusion device body 21 could contain a compressed gas chamber rather than a vacuum chamber 20. Such a compressed gas chamber would typically be located on the proximal side of the sliding sealed piston 42, between the sliding sealed piston 42 and the ported base 26. This would require a fluid tight seal on the proximal aspect of the chamber near the ported base 26 and alignment guide 28. Another compressed gas force energizer could include a compressed air cartridge removably attachable to such a compressed gas reservoir and provide a force proportionate to the difference between the pressure within the compressed air source and atmospheric pressure. If this compressed air supply is sufficiently high in pressure, as the driver 50 would move, along with any sliding sealed piston 42 coupled thereto, the pressure differential would reduce slightly relative to atmospheric pressure but would be sufficiently small that a substantially constant force would be applied to the syringe S. Other analogous alternative resistance force energizers could also be provided.

The resistance force energizers (vacuum chamber 20, spring, compressed gas, etc.) will tend to hold the force applicator 40, 50 at its resting point, but can also act as an energy storage device when the force applicator (arm 40 and driver 50) section is locked out in some degree of excursion and temporarily held there by an interaction between the arm 40 and the infusion device base 26. In the preferred embodiment, such locking of the arm 40 relative to the base 26, through interaction of the facets 46 on the arm 40 with the faceted alignment guide 28 of the body 21 causes potential energy to be stored equivalent to the resistant force that is applied to the arm 40 multiplied by the distance that the force applicator (arm 40 and driver 50) and sliding sealed piston 42 have been translated outward (excursion). In the case of a spring, the potential energy is the distance traveled by the spring when the arm 40 or similar structure is able to move, multiplied by the spring force for the spring.

With particular reference to FIGS. 2, 3, 5, 6, 8 and 9, details of the stopcock valve 60 according to a preferred embodiment are described. In some of these embodiments (FIGS. 2, 5 and 8), a manifold hub 70 is provided according to the most preferred embodiment. In other figures (FIGS. 3, 6 and 9) an alternative manifold hub 170 is provided. For each of these stopcock valves 60, a common housing 62 is provided.

This housing 62 is generally a short hollow cylinder in form which is open on one side so that it has a recess 64 therein which is generally cylindrical and generally with a diameter greater than a depth thereof. This recess 64 has its periphery defined by a wall of the housing 62 which is generally cylindrical and includes the ports A, B, C, D therein, preferably each in a common plane spaced 90° away from each other and extending radially away from a central axis of the housing 62.

As an alternative, only three ports could be provided (one for a source of medicament, such as the second syringe T or vial adapter 90, one for the syringe S and one for the patient infusion interface 84). Preferably, the ports A, B, C, D are generally cylindrical in form with central axes thereof extending radially away from a central axis of the housing 62 and with the ports A, B, C, D and housing 62 all formed together or rigidly attached together as a single construct.

The manifold hub 70 resides within the recess 64 and provides for fluid access between at least two of the ports A, B, C, D depending on the orientation of the manifold hub 70 within the recess 64. This manifold hub 70 is preferably substantially cylindrical in form and has a size and shape which allows it to fit snugly within the recess 64, but with rotation allowed about a central axis of the housing 62 (along arrow I of FIGS. 2-10). This manifold hub 70 includes a selector 72 in the form of an arm which is preferably raised from a face 73 and extends beyond a perimeter of the manifold hub 70. The selector 72 can be grasped manually and turned to set the valve 60 as desired.

The manifold hub 70 can be hollow or solid but is particularly characterized by one or more fluid flow paths contained therein. Most preferably, the manifold hub 70 includes a central fluid flow path 74 which extends linearly and radially through the manifold hub 70, so that it can align ports A, C or ports B, D which are opposite each other directly together when the central fluid flow path 74 is aligned with such ports A, C or ports B, D.

However, in a most preferred embodiment, the tolerances followed in forming the manifold hub 70 and the housing 62 are preferably sufficiently tight that the manifold hub 70 is prevented from undesirable rotation within the housing 62, and also a fluid tight fit is accomplished. Other techniques for leak prevention or mitigation can also be utilized, as is known in the art, for such valves.

In the manifold hub 70, a preferred orientation of additional fluid flow paths demonstrates a first side leg 76 and a second side leg 78 are also provided which extend radially from a center of the manifold hub 70 and at angles 90° spaced from each other and 45° spaced from ends of the central fluid flow path 74. With such a configuration, the first side leg 76 and second side leg 78 can be aligned with adjacent ports A, B, C, D for passage of fluid between any two adjacent ports A, B, C, D depending on the position of the manifold hub 70, as controlled by gripping and rotation of the selector 72 (along arrow I).

With particular reference to FIGS. 3, 6 and 9-13, details of an alternative manifold hub 170 are described. This alternative manifold hub 170 is preferably similar to the manifold hub 70 except that fluid fluid flow paths therein are routed somewhat differently. In particular, a selector 172 and face 173 are similar to those of the manifold hub 70. A first fluid flow path 174 is provided which is linear and extends radially through a middle of the alternative manifold hub 170 with no intersections at midpoints thereof. A second fluid flow path 176 is also provided which is positioned lateral and parallel with the first fluid flow path 174, but is laterally spaced from the first conduit 174. A version of the second flow path 176, which is not shown, may be non linear and skirting along the periphery of the manifold hub 170, but having openings on each side that would coincide with those shown on the second fluid flow path 176. Sleeves 175 can be provided as depicted in FIG. 11.

The second fluid flow path 176 is positioned so that ends thereof are spaced 45° away from ends of the first fluid flow path 174. Thus, ends of the first fluid flow path 174 and second fluid flow path 176 are similarly placed as ends of the central fluid flow path 74 and legs 76, 78 of the manifold hub 70 (FIGS. 2, 5 and 8). By rotation of the manifold hub 70, 170 relative to the housing 62 (along arrow I of FIGS. 2-10), ends of the fluid flow paths 74, 76, 78, 174, 176 can be brought into alignment with various different ports A, B, C, D to route medical preparations or other fluids through the stopcock valve 60 in a manner desired.

Preferably, the face 73 is printed with indicia which provide an indication as to where these fluid flow paths are within the manifold hub 70, 170. Preferably, the selector 72 is provided extending radially at a location spaced from this indicia so that the selector 72 does not block the indicia from being easily viewed by a user. A user merely orients the indicia so that they are aligned with the ports A, B, C, D which the user desires to have brought together into fluid communication, and then the manifold hub 70, 170 is set properly for proper operation of the stopcock valve 60. Such indicia are also useful in allowing a medical professional to, at a quick glance, verify that the stopcock valve 60 is set at the proper position, such as when inspecting a patient's care regimen.

In use and operation, and with particular reference to FIGS. 14-18, details of the operation of the infusion device 10 are described, according to a preferred embodiment. Initially, a user has the option of first snapping the infusion device 10 onto the syringe S (arrow F of FIG. 1) or first charging the chamber 20 with a vacuum by excursion (movement of the driver 50, arm 40 and associated sliding sealed piston 42 proximally out of the chamber 20) of the force applicator via its handle 58, as shown in FIG. 14. Upon such movement, a vacuum is drawn within the chamber 20 and potential energy is induced, yielding a state of "activation." If some time will elapse before the infusion device 10 will be utilized or if a pause is required, the force applicator may be reversibly disabled while in this activated state. This disabling requires the handle 58 of the driver 50 to be rotated (arrow G of FIGS. 4 and 15) so that the facets 46 on the arm 40 no longer are aligned with the facets on the faceted alignment guide 28. Thus, when the handle 58 of the driver 50 is released, and the vacuum pulls (actually the atmosphere pushes) the arm 40 toward the vacuum chamber 20 distally, the facets 46 on the arm 40 abut the faceted alignment guide 28 in this nonaligned disabling configuration to prevent further movement of the arm 40 into the chamber 20. This activated but disabled configuration allows the device to store the potential energy. Other potential mechanisms exist for disabling the force applicator while activated including a pin or sliding plate that could be reversibly attached to the arm at various positions but not being able to traverse through the alignment guide, thereby halting incursion of the arm and infusion.

By providing four facets 46 on the arm 40 and four facets on the faceted alignment guide 28, and a generally square cross-section for each, rotation of the arm 40 (along arrow G) 45° from the disabled configuration about a central axis thereof will cause the infusion device 10 to transition back from a disabled potential energy storage orientation to an enabled energy delivering force applicator (and vice versa).

Such rotation of the arm 40 (about arrow G of FIGS. 4 and 15), can both be used to put the infusion device 10 into a potential energy storage orientation, but also can be utilized to provide clear access to the plunger P of the syringe S or to engage the driver 50 of the infusion device 10 with the proximal terminus H of the plunger P of the syringe S. For instance, after the infusion device 10 has been snapped on to the syringe S (arrow F of FIG. 1) and after a vacuum has been drawn on the chamber 20 (by movement along arrow E of FIGS. 4 and 14) and after the arm 40 has been rotated slightly (about arrow G of FIG. 15) while the neck 45 of the arm 40 is aligned with the faceted alignment guide 28, so that the infusion device 10 is in a potential energy storage orientation, the piston P of the syringe S can still be easily accessed. In such an orientation, a user can load the syringe S in a typical fashion, such as by pulling on the proximal terminus H of the plunger P to cause medicament to be drawn into the syringe. Such a loading of the syringe S can occur with medicament being supplied from another syringe such as the second syringe T, or from a medication vial M, or from some other source coupled to the stopcock valve 60 through one of the ports A, B, C, D. As another alternative, the syringe S could be a preloaded syringe or it could be loaded from a proximal end, or it could be removed from the stopcock valve 60 altogether and loaded in some other fashion.

Once the syringe S has been loaded and is ready for infusion, the arm 40 is further rotated so that the driver 50 can be aligned with the proximal terminus H of the plunger P of the syringe S. The driver 50 is then released slightly until the engagement plate 52 abuts the proximal terminus H of the syringe S. Force is now being applied to the plunger P of the syringe S and medicament is being delivered from the syringe S and through the stopcock valve 60 and into the patient through the patient interface section and its connector 84.

The stopcock valve 60 would first be rotated appropriately (along arrow I) so that fluid flow would occur toward the patient interface section 80, 82, 84. Such force application occurs along arrow K of FIGS. 7 and 16. Because the force occurs at a constant rate, as the force associated with the vacuum remains constant, a constant force is applied to the syringe S for delivery of the medicament at a constant rate. This force can be modified by modifying a volume of the chamber 20, such as by modifying a diameter of the chamber 20. Thus, different size infusion devices could be provided having different forces and hence different flow rates. As another alternative, the regulator 80 can be utilized for such flow rate regulation. Other flow restrictions at other locations, including at an interface between the syringe S and the stopcock valve 60 or as a function of the tubing itself could also alternatively be utilized for such infusion rate control.

If a user desires to provide an additional surge of medical preparation into the patient through the patient interface 80, 82, 84, a medical professional can merely push on the handle 58 of the driver 50 to enhance the force that is otherwise being provided by the interaction of the atmosphere and the vacuum chamber 20 (or they could change the flow direction through the stopcock valve 60 to exit another port with a decreased or absent flow regulator 80). Similarly, infusion can be temporarily or permanently stopped by merely pulling on the handle 58 of the driver 50 (along arrow B of FIG. 14) in the middle of an infusion process to pull the driver 50 off of the proximal terminus H of the plunger P of the syringe S, until the neck 45 of the arm 40 is aligned with the faceted alignment guide 28. Then, the force activator with its arm 40 can be rotated slightly (along arrow G) to cause energy storage once again. The syringe S will then sit idle and disabled with no medicament infusing until the infusion device 10 is again positioned with the driver 50 acting on the proximal terminus H of the plunger P of the syringe S. Thus for instance, if the patient interface 80, 82, 84 requires adjustment, the infusion device 10 can be easily stopped and restarted in the midst of infusion. The infusion process may also be readily discontinued by truly deactivating the force activator. This deactivation discontinues infusion as well and is accomplished by pulling the force activator back to its neck, rotating it (and its arm 40) a full 90° or 180° in either direction to another corresponding faceted position (where the faceted arm may again undergo incursion through the faceted alignment guide, but with incursion occurring where the engagement plate will not interact with the syringe proximal terminus) where the force activator can be let down to its resting point thereby releasing the stored potential energy and stopping the infusion process.

Figure 22:
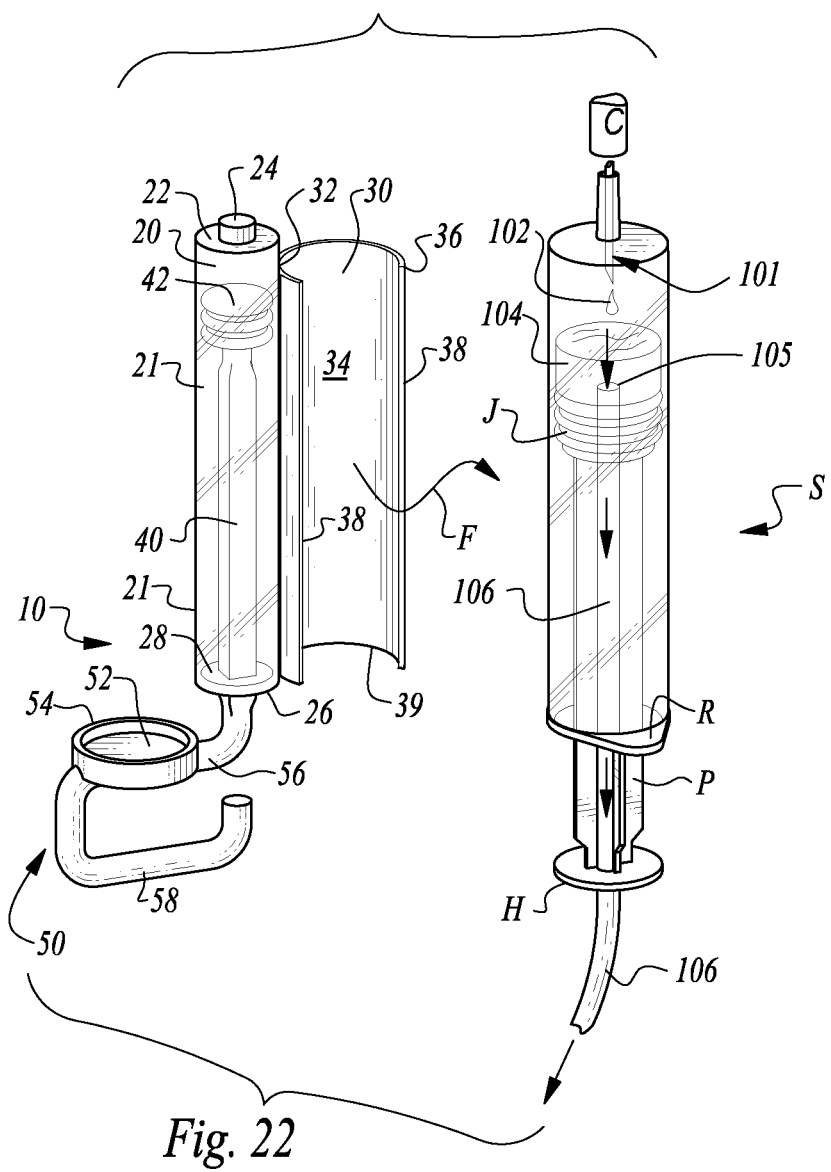
FIG. 22 is a perspective view demonstrating the infusion system medicament syringe being integrated into a disposable intravenous administration set (commonly utilized in the practice of IV administration which connects the fluid to be infused with the IV catheter in the patient's vein) where it may accomplish the goals set forth in this disclosure, but with a step saved as it allows the infusion device to be already integrated into the "intravenous administration set," thereby not requiring connection. This arrangement may allow a solitary integration or it may be placed in the position of the "drip chamber" and utilized for both functions (infuser and drip chamber), if so desired by the manufacturer or practitioner. This integration is shown with the syringe in the position of the drip chamber thereby acting as the drip chamber and as a syringe adapted to infuse. The infuser is positioned lateral to the syringe but not connected in this figure.

FIG. 22 demonstrates an infusion syringe S "built in" to a typical disposable intravenous (IV) administration set. The syringe S is placed proximally in the set in an "inline" configuration and in this embodiment also takes the place of the "drip chamber" which is typically present in the prior art administration sets.

The FIG. 22 preferred embodiment shown demonstrates the IV fluid flow path which would deliver the IV fluid from a plastic bag into the stopcock (not shown, but from stopcock port A to port C) and into the syringe S via the port at the distal tip (stopcock port C would typically be directly connected to the port at the syringe distal tip, but for clarity, it is shown adjacent in this figure). The IV fluid would enter the syringe tip through an embedded "drip needle" 101, so that dripping IV fluid 102 could be visualized and quantified by counting drips per minute as it drips into the medicament reservoir 104. The IV fluid or medicament in the medicament reservoir 104 exits via a second port called the piston fluid conveyance port 105 (positioned on the syringe piston J and allowing fluid conveyance through the piston J and into the IV fluid tubing 106 where it may traverse down along the syringe plunger P (or within the plunger P) through further IV fluid tubing 106 and eventually into the patient's vein). This embodiment would save the practitioner the trouble of locating a separate syringe for medicament delivery as it would already be present in the IV administration set where it could be utilized in similar fashion to descriptions of this invention noted elsewhere in this disclosure.

Figure 23:
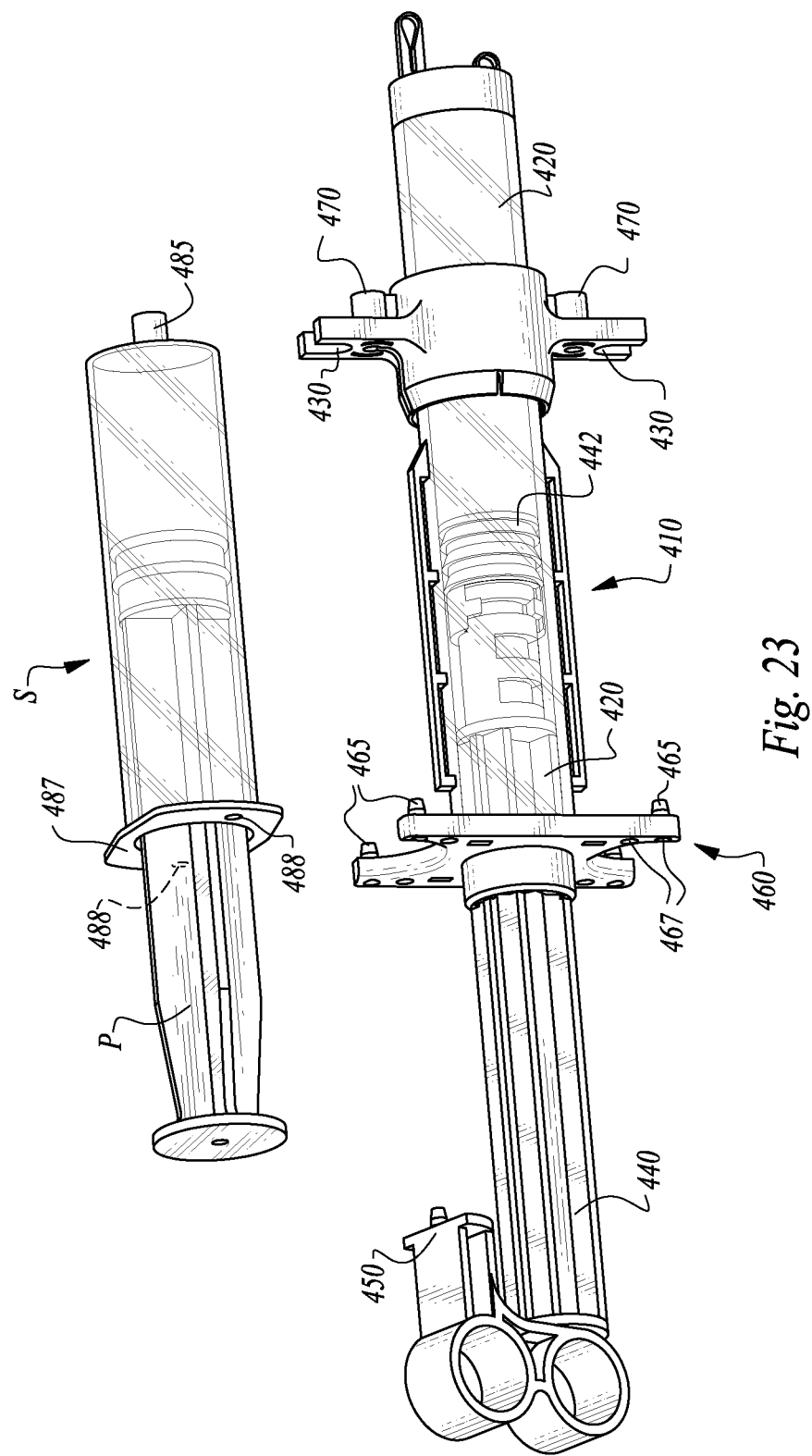
FIG. 23 is a perspective view of an infuser and syringe provided according to an alternative embodiment of the invention of this application, featuring a clamp assembly and retainer structure for holding the syringe to the infuser.
Figure 24:
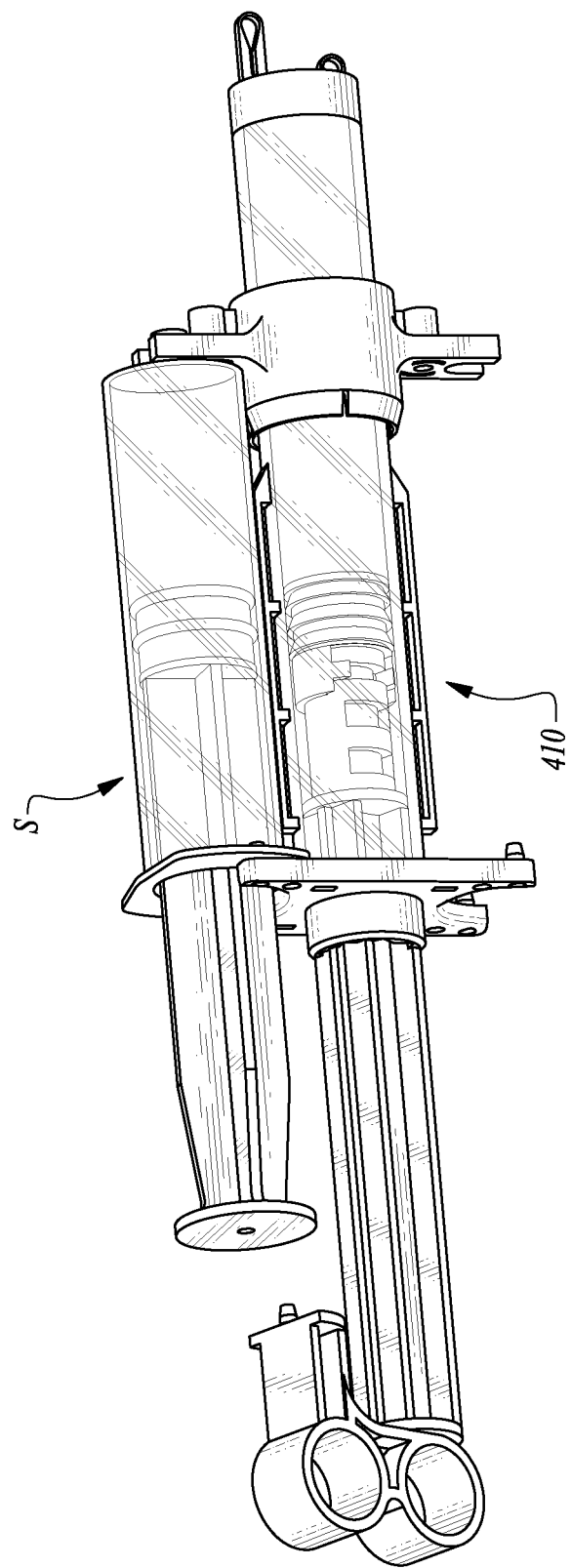
FIGS. 24-28 are perspective views of the infuser and syringe of FIG. 23 in various different stages of interfacing together, and action of the infuser upon the syringe to drive fluids out of the syringe according to a method of this invention.
Figure 25:
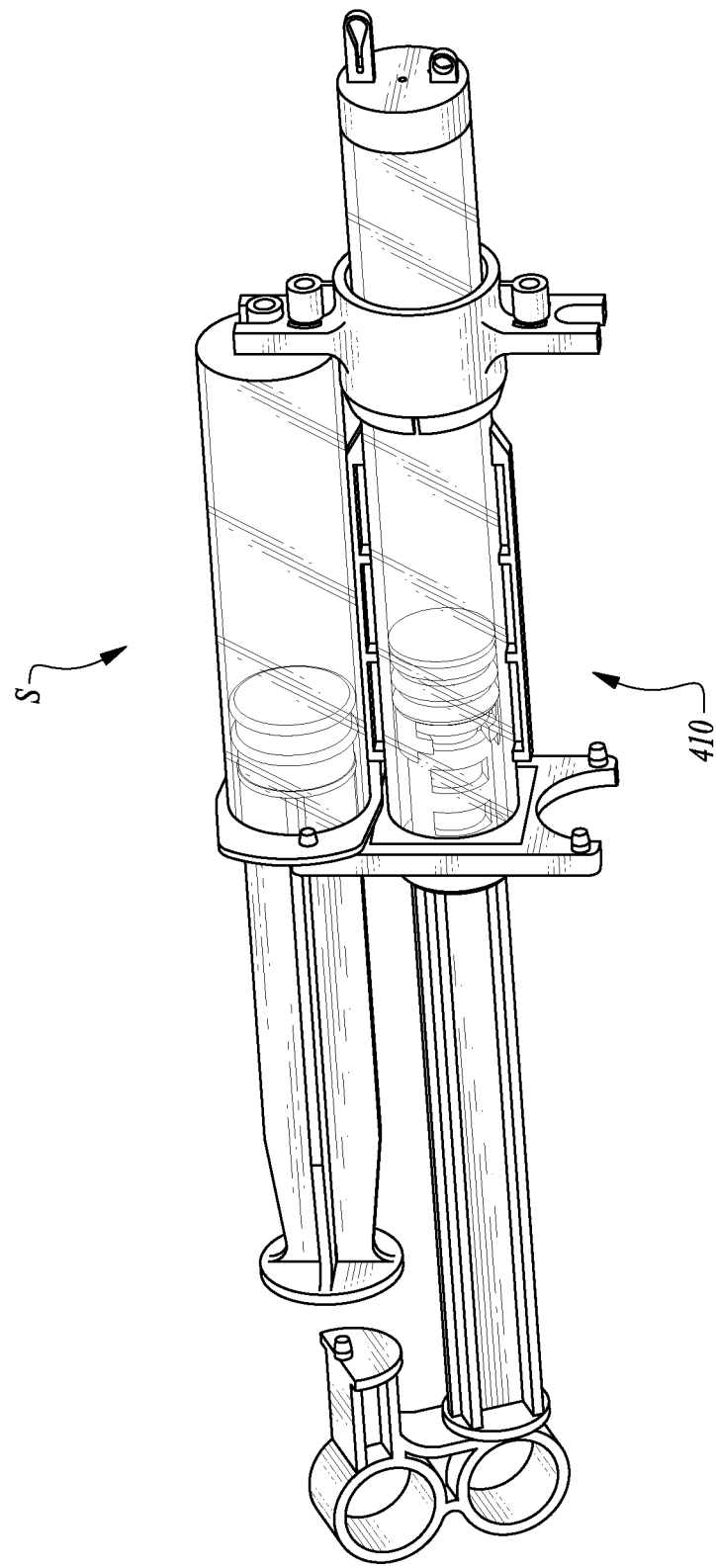
Figure 26:
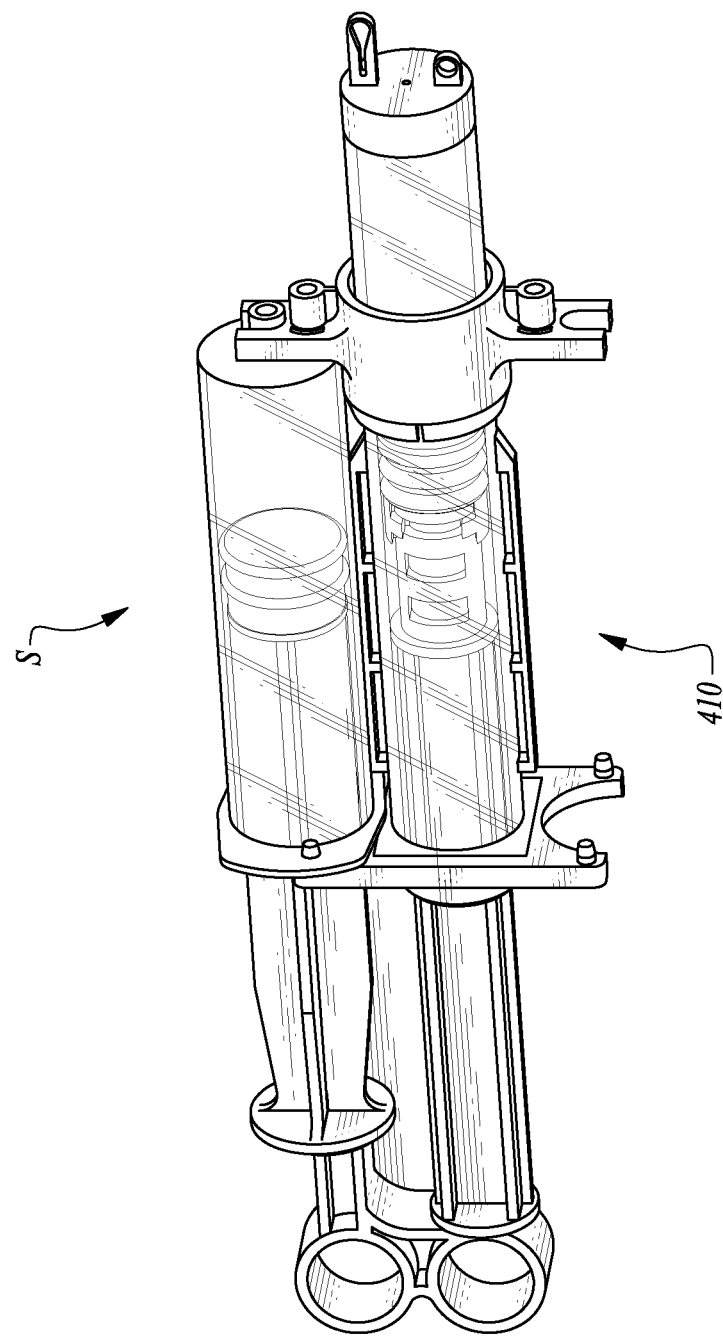
Figure 27:
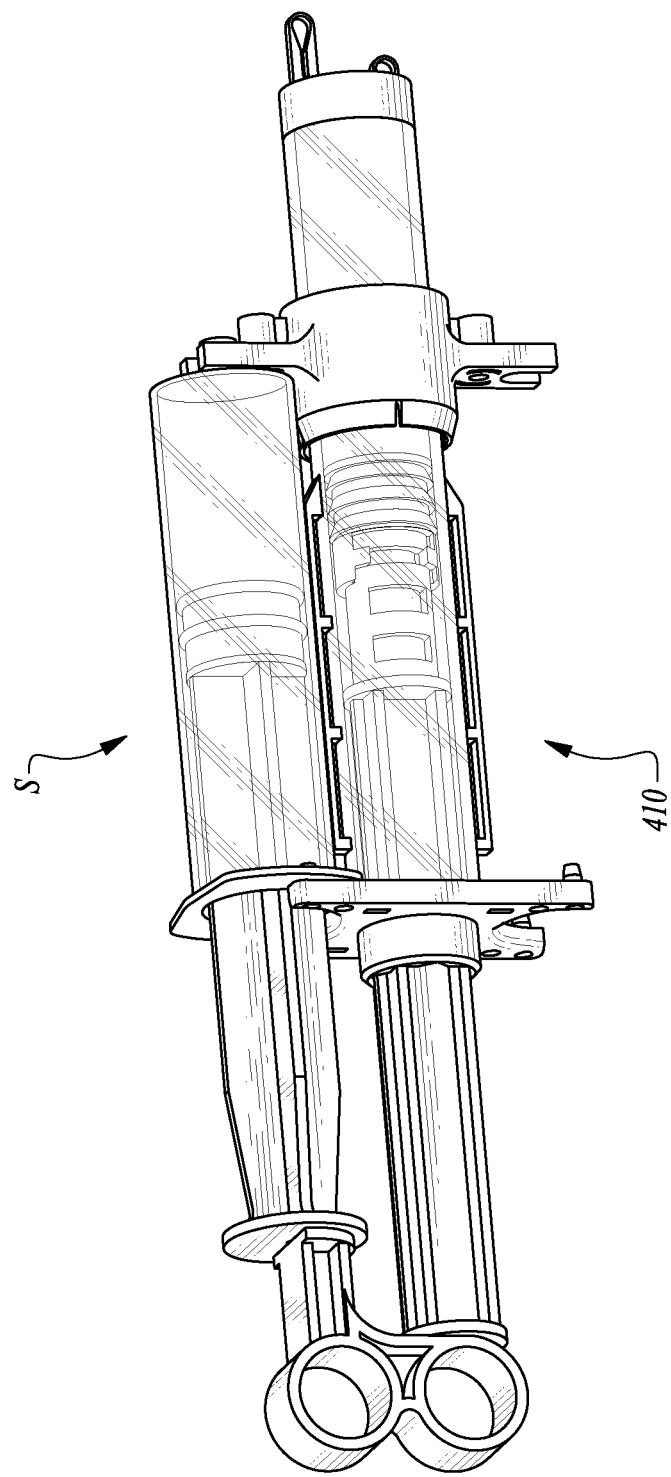
Figure 28:
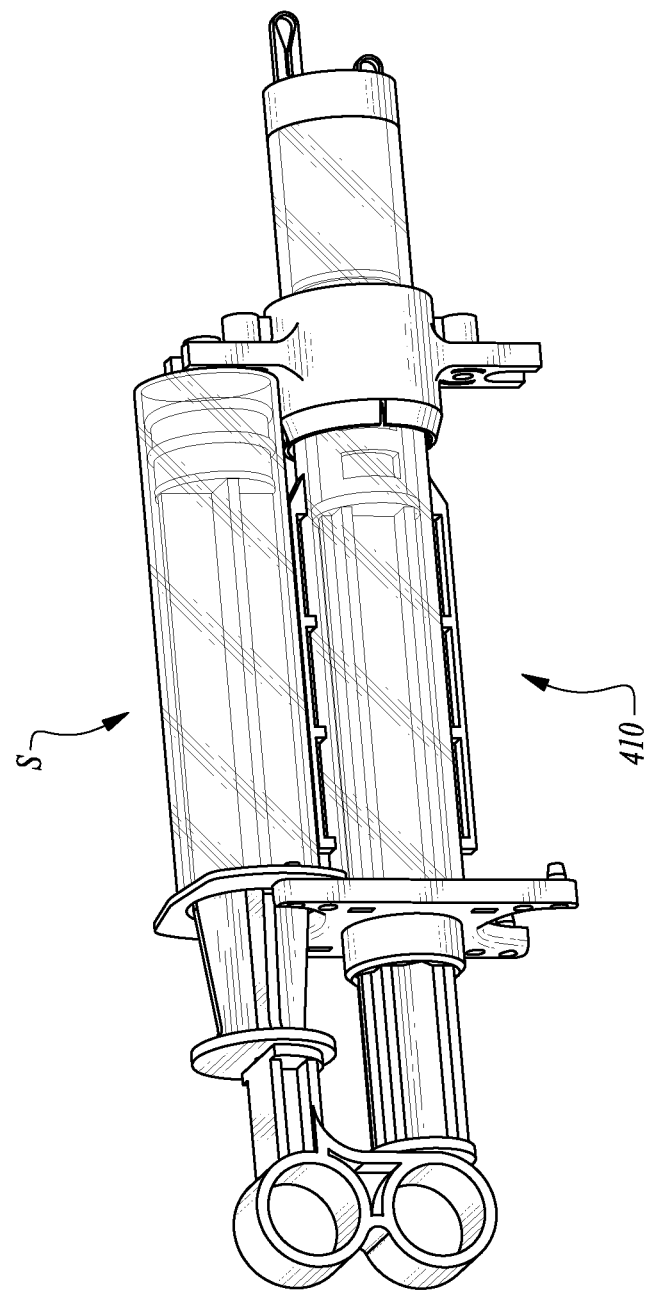

With reference to FIGS. 23-33, details of a specific embodiment of the infuser 410 of this invention are disclosed along with an exemplary syringe S in practicing the system and method of this invention. Referring to FIG. 23 primarily, an infuser 410 is depicted which includes a chamber 420 in which a vacuum can be drawn. A piston 442 translates within the chamber 420 and is coupled to an arm 440 which extends out of the chamber 420. A driver 450 is located on an end of the arm 440 opposite the piston 442. A clamp 430 assembly is located closer to a distal end of the chamber 420 with a retainer 460 located closer to a proximal end of the chamber 420. The clamp 430 assembly and retainer 460 act together to removably couple the infuser 410 to a syringe S.

The clamp 430 assembly preferably has multiple stations which can support a separate syringe S. Each station preferably includes a clamp 430 which is sized to allow an outlet end of the syringe S to snap thereinto. A boss 470 is preferably located adjacent each clamp 430 with the boss 470 sized similar to the outer periphery of the outlet of the syringe. In this way, a clamp 430 can either snap onto an outlet 485 end of the syringe S or onto a boss 470 of an additional infuser 410 (see for instance FIG. 32).

The retainer 460 also includes multiple stations with a number of stations provided on the retainer 460 generally corresponding with the number of stations provided on the clamp 430 assembly and with such retainer 460 stations aligned with the clamp 430 stations. Each retainer 460 station has a semi-circular saddle which can cradle a portion of the cylinder 486 of the syringe S therein adjacent to a flange 487 of the syringe S.

The flange 487 of the syringe S preferably includes holes 488 therein which are sized and spaced from each other a distance similar to a distance between prongs 465 on the retainer 460 associated with each station and near ends of the saddle. The prongs 465 can reside within the holes 488 so that the flange 487 of the syringe S is held securely to the infuser 410. A side of the retainer 460 opposite the prongs 465 preferably includes a series of bores 467 therein which are spaced apart a distance similar to a distance between the prongs 465. In such an arrangement, the prongs 465 can optionally reside within bores 467 of an adjacent separate infuser 410 (see for instance FIG. 32) to allow two infusers 410 to be attached together.

The arm 440 and driver 450 of the infuser 410 are adapted to translate relative to remaining portions of the infuser 410 with the driver 450 able to engage with a proximal end of a plunger P of the syringe S to apply a force on the plunger P tending to drive fluid out of the outlet 485 of the syringe S. A passage through the retainer 460 allows the arm 440 to pass therethrough in a manner that allows translation of the arm 440 but resists rotation of the arm 440. The arm 440 has a contour which matches the contour of this passage through the retainer 460 except at a section on the arm 440, preferably near the piston 442, where the arm 440 has a differing cross-section which facilitates rotation of the arm 440. The particular geometry for such structures is depicted in FIG. 23.

Figure 29:
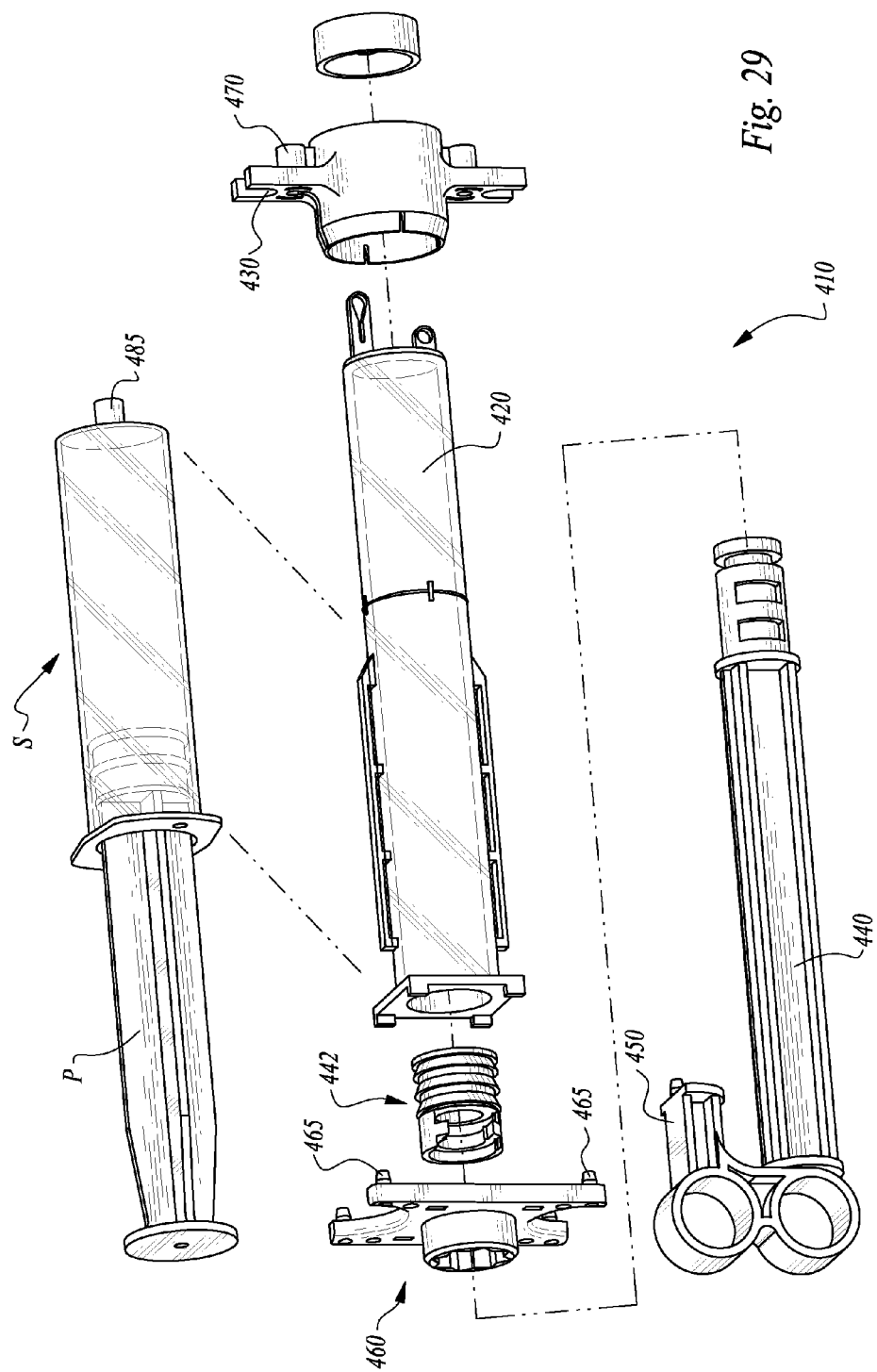
FIG. 29 is an exploded parts view of that which is shown in FIG. 23.

FIGS. 24-28 reveal a series of steps associated with aligning the arm 440 and driver 450 of the infuser 410 with the plunger P of the syringe S and acting over time to efflux fluid out of the outlet 485 of the syringe S as the piston 442 is drawn into the chamber 420 of the infuser 410 to replace the vacuum contained therein. FIG. 29 is an exploded parts view of that which is shown in FIGS. 23-28.

Figure 30:
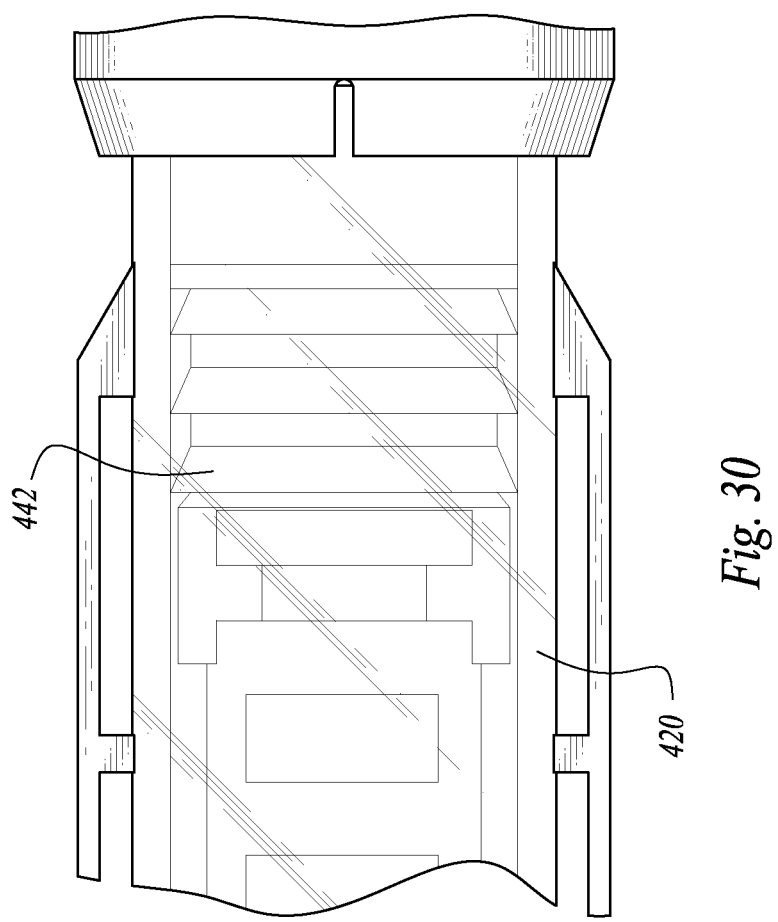
FIG. 30 is a detail of a portion of that which is shown in FIG. 23 revealing details of a system featuring one-way biased O-rings.
Figure 31:
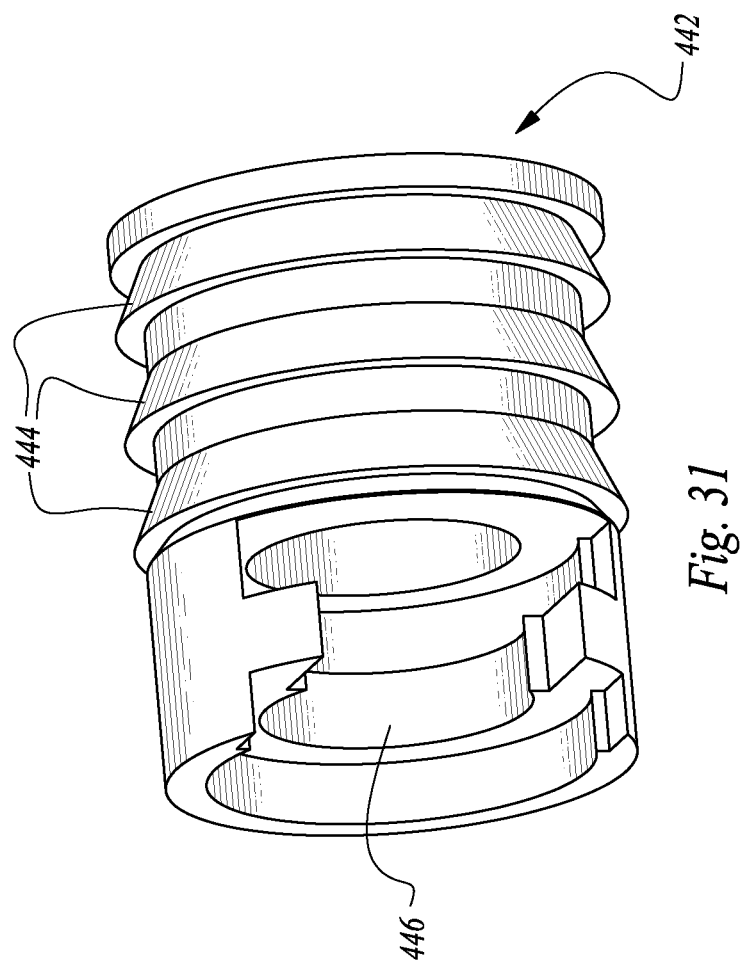
FIG. 31 is a perspective view of the driver with one-way biased O-rings shown separated from other portions of the infuser.

The piston 442 preferably has a specific configuration such as that depicted in FIGS. 30 and 31. The piston 442 is preferably fitted with a series of O-ring 444 type seals which are biased. With such a bias, air is allowed to pass more readily past the piston 442 and toward the arm 440 than past the piston 442 and away from the arm 440. With such a biased configuration for the O-rings 444, the piston 442 and associated arm 440 can be readily inserted into the chamber 420 during initial assembly without compressing air against the distal end of the housing. As the piston 442 is initially driven into the chamber 420, air originally within the chamber 420 is able to pass the biased O-rings 444 to exit the chamber 420. Once the piston 442 has been driven all the way to the distal end of the chamber 420, the infuser 410 is then in a configuration ready for operation. When the piston 442 is later translated toward the proximal end of the chamber 420 and away from the distal end of the chamber 420, air cannot pass the biased O-rings 444 so that a vacuum is drawn within the chamber 420 at the distal end thereof. Such a piston 442 with biased O-rings 444 eliminates the need for a port at the distal end of the chamber 420 for initial piston 442 positioning.

Figure 32:
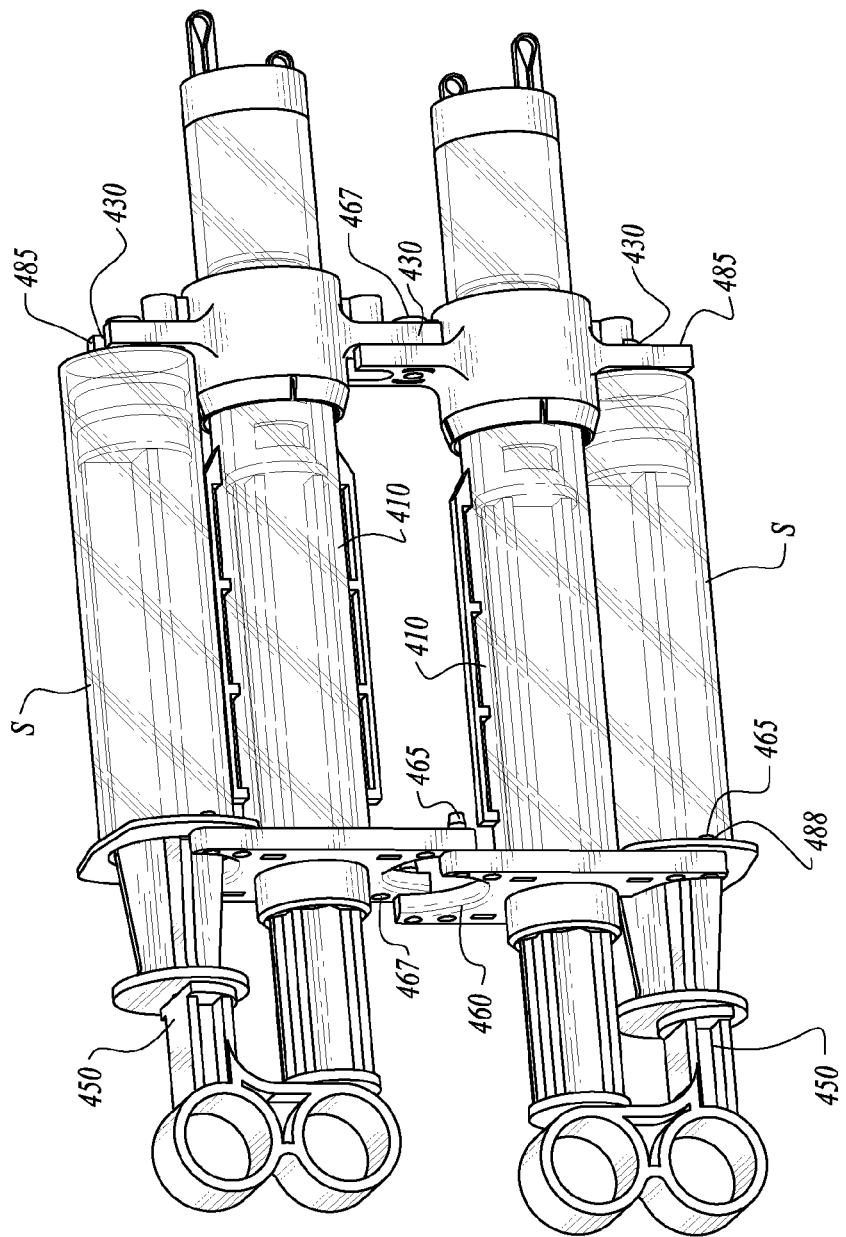
FIG. 32 is a perspective view of a pair of infusers and a pair of syringes all assembled together illustrating one assembly which can be configured utilizing the infuser and syringe of this invention.

With particular reference to FIG. 32, an assembly is depicted which utilizes a pair of infusers 410 and a pair of syringes S. The two infusers 410 have been coupled together utilizing the clamps 430 and bosses 470 of the clamp 430 assemblies and the prongs 465 and bores 467 of the retainers 460. Each infuser 410 is also coupled to a syringe S in the manner depicted in FIGS. 23-28. Such interconnection of the infusers 410 can be useful where more than one medication is to be infused simultaneously, so that separate syringes S are provided with separate medications. With the infusers 410 able to be coupled together, a single assembly is provided for delivery of two or more such medications.

Figure 33:
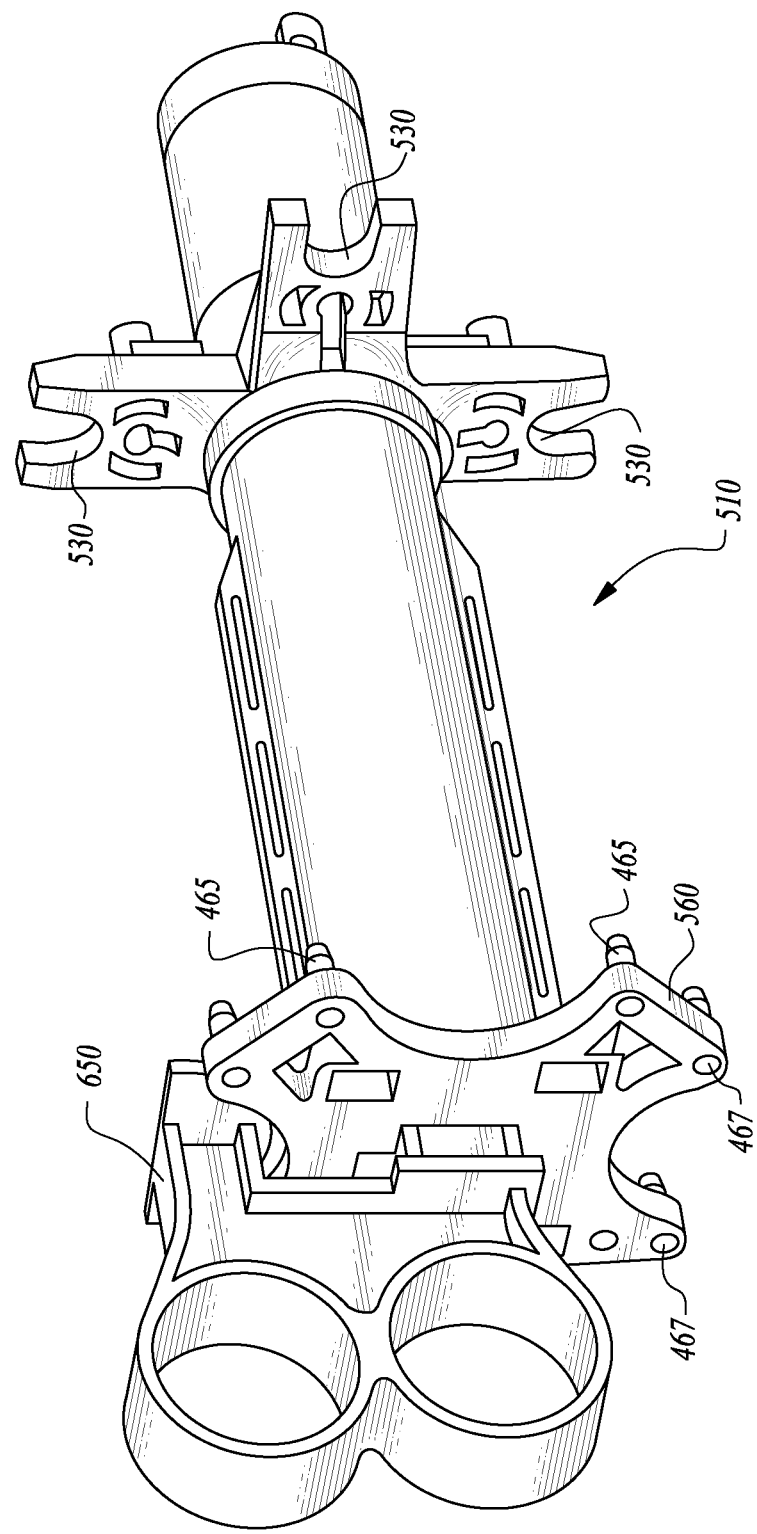
FIG. 33 is a perspective view of an alternate infuser which has a clamp assembly and retainer structure which are configured to facilitate attachment of three syringes to a single infuser.

Furthermore, and with reference to FIGS. 23-28, it can be seen that preferably at least two stations are provided on each clamp 430 assembly and each retainer 460. Hence, two syringes S can be coupled to a single infuser 410. According to one use of the infuser 410 of this invention, two syringes S loaded with medication can be coupled to separate stations on the infuser 410. The infuser 410 can be set to begin infusing from one syringe S. When medication within the first syringe S has been entirely dispensed, the infuser 410 can be recharged by pulling the piston 442 and arm 440 out of the chamber 420 and rotating the arm so that the driver 450 is aligned with the second syringe S and then medication from the second syringe S can be dispensed. Thus, a potential for an overall singular assembly which has twice the capacity is facilitated. If three or more stations are provided on the clamp 430 assembly and retainer 460 of each infuser 410, three or more syringes S can be included in such an overall assembly. With reference to FIG. 33, an infuser 510 is depicted which exhibits three such stations on a clamp 530 assembly and on a retainer 560 to illustrate how such a multi-station infuser 510 could be configured according to this embodiment.

While the infuser 410 is depicted with a vacuum chamber 420, as an alternative a spring could be interposed between the arm 440 of the infuser 410 and the chamber 420 or infuser body replacing such a chamber 420. In one embodiment this spring could be a helical compression spring located within the chamber and generally between the proximal side of the piston 442 and the retainer 460. The chamber 420 could still be provided to allow the spring to operate within a controlled environment. Similarly, a helical tension spring could be interposed between a distal end of the arm 440 and a distal end of the chamber 420, or other distal end of the infuser 410.

Figure 36:
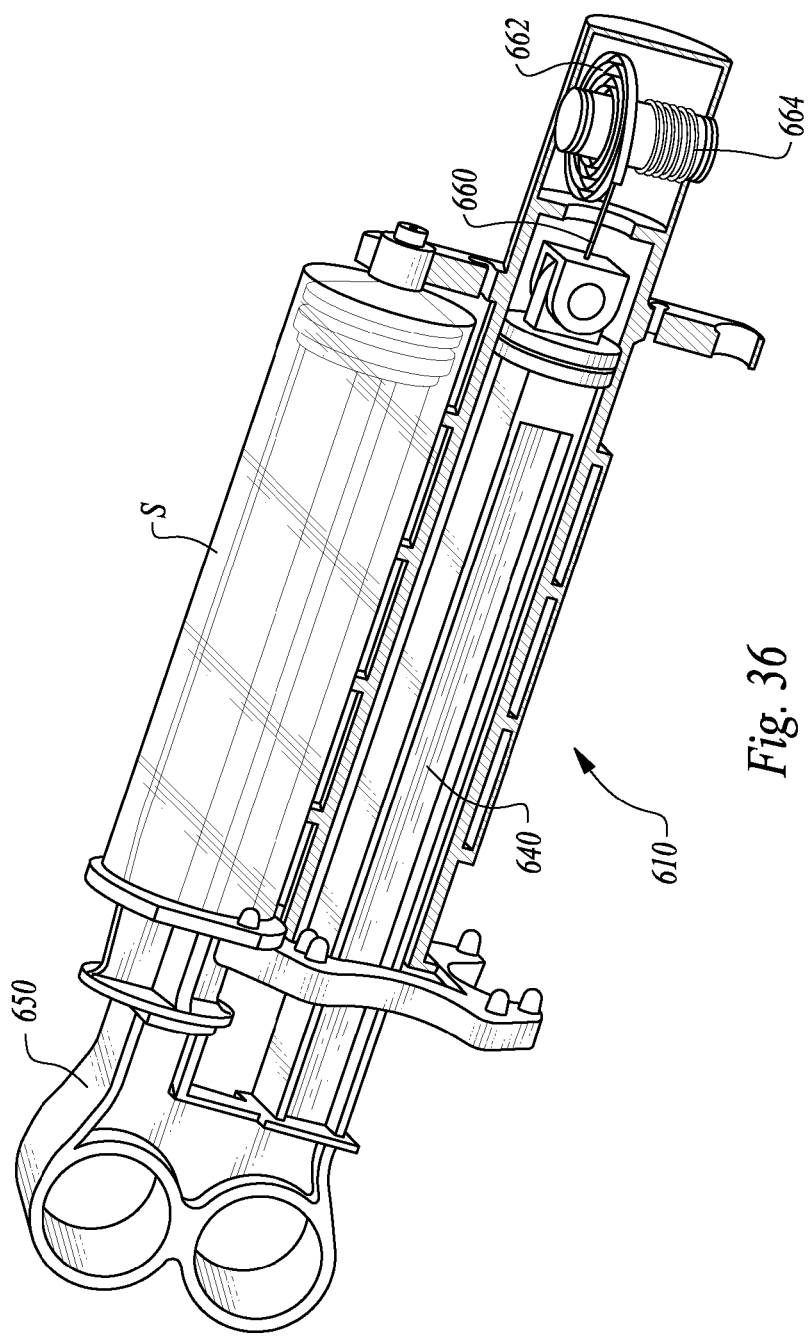
FIG. 36 is a perspective view of an alternative embodiment torsion spring driven infuser and associated syringe.

With particular reference to FIG. 36 details of a torsion power spring driven infuser 610 are described, according to an alternative embodiment. The torsion power spring driven infuser 610 includes a torsion spring 662 mounted about a central shaft which also acts as a spool 664 upon which a cable 660 can be gathered. This cable 660 extends from the shaft and associated spool 664 at a distal end to an arm 640 attachment point at a proximal end. The torsion power spring 662 exerts a rotative force upon the shaft tending to cause the shaft to rotate and for portions of the cable 660 to be gathered upon the spool 664. In turn, this tension on the cable 660 causes an energizing tension force to be maintained on the arm 640 which in turn causes the driver 650 to act upon a plunger of the syringe S to drive the plunger into the syringe S and deliver fluid out of the syringe S.

The torsion power spring 662 is caused to have energy stored and the spring 662 to be wound by having the arm 640 and driver 650 pulled away from the torsion spring 662. This energy can be stored on the spring 662 until needed. Then, when the driver 650 is coupled to a plunger of the syringe S and the arm 640 released from any engagement structures which lock the arm 640 in position, the arm 640 is caused to be drawn towards the central shaft of the torsion spring 662 to provide the infusion force. An infusion rate is provided which correlates with a spring force of the torsion spring 662 and to resistance to fluid flow associated with the syringe S and downstream structures such as microbore tubing, flow rate control elements and any friction built into the system.

The holes 488 in the flange 487 of the syringe S are preferably configured to match an arrangement of prongs 465 on the retainer 460 of the infuser 410. Such coordination of holes 488 and prongs 465 can include the position of the holes 488 and prongs 465, the number of holes 488 and prongs 465, and the location of the holes 488 and prongs 465. In addition to stabilizing the syringe S relative to the infuser 410, such a particular configuration for the holes 488 and prongs 465 can act to coordinate syringes S of a particular style with infusers 410 of a particular style. For instance, infusers 410 having different rates of infusion and different amounts of force applied can be produced, such as by changing a diameter of the chamber 420. Different medications have different desired rates of infusion. Syringes S preloaded with a medication having a desired rate of typical infusion could be configured with a hole 488 pattern on the flange 487 which would correspond with the prong 465 pattern on an infuser 410 which provides the desired infusion rate. Such coordination assists a user in matching a proper infuser 410 with the proper syringe S and medication.

While the holes 488 and prongs 465 are shown on the flange 487 and retainer 460 respectively, the prongs 465 could be provided on the flange 460 of the syringe S and holes 488 provided on the retainer 460. While the prongs 465 and holes 488 are each shown with a circular cross-section they could have differing shapes which would not fit unless the proper syringe S is mated with the proper infuser 410. Furthermore, even with standard syringes S and infusers 410 it is desirable that the holes 488 and prongs 465 act together to securely hold the flange 487 of the syringe S adjacent the infuser 410. By matching configurations of the prongs 465 and holes 488, a quality control feature is also provided in that syringes S and infusers 410 which have been manufactured to the desired quality standards interface together while syringes S and infusers 410 of differing quality standards and without the authorized prong 465 and hole 488 configuration would not match together, such that the quality expectations of the user can be met.

Figure 34:
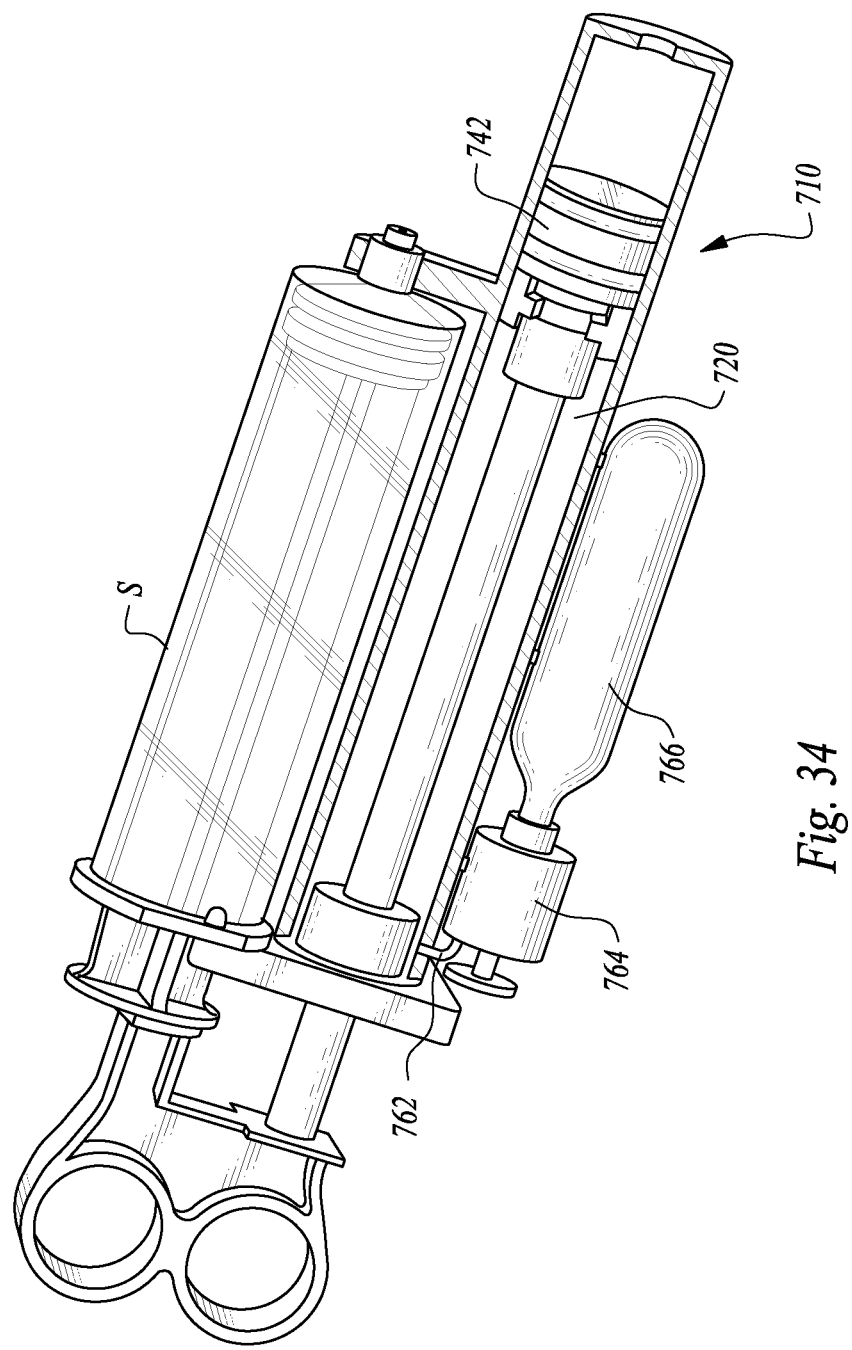
FIG. 34 is a perspective view of an alternative embodiment gas driven infuser and associated syringe.

With reference to FIG. 34, details of an alternative embodiment gas driven infuser 710 are described. With this gas driven infuser 710, the chamber is fitted with a piston 742 with associated arm. However, a distal end of the chamber 720 is not sealed and not configured to contain a vacuum. Rather, a proximal end of the chamber 720 is enclosed and has a feed line 762 associated therewith which leads to a control valve 764 to which a $CO_2$ gas cartridge 766 or other gas cartridge 766 can be attached. Typically this cartridge 766 is removably attached to the control valve 764. One configuration could be similar to that utilized in paintball marker compressed $CO_2$ gas firearms.

The control valve 764 acts as a regulator which can selectively allow compressed gas to pass into the housing 720 through the feed line 762. Through calibration and control of design details such as a friction of the piston 742 as it slides within the housing 720, and an amount of resistance to flow associated with an outlet of the syringe S and/or downstream resistance such as within microbore tubing or other flow restriction devices, a rate at which the gas driven infuser 710 operates can be controlled.

As an alternative, a more active control can be utilized which causes the control valve 764 to open and close appropriately depending on whether a rate of infusion is faster or slower than a desired rate. Such a basic control system would keep track of a position of the plunger within the syringe S and keep track of time and increase or decrease openness of the control valve 764 depending on whether a sensed rate of infusion is faster or slower than a desired rate.

A bleed port would typically be built into the control valve 764 which would allow for the piston 742 to return to a proximal end of the housing 720, such as after infusion of fluid from the syringe S has been completed and it is desired to reset the infuser 710 with a new loaded syringe S. One advantage of such a gas driven infuser 710 would be its ability to operate consistently in environments having different pressures, such as at different altitudes within Earth's atmosphere or potentially underwater or in space where pressures radically diverging from atmospheric pressure are experienced.

Figure 35:
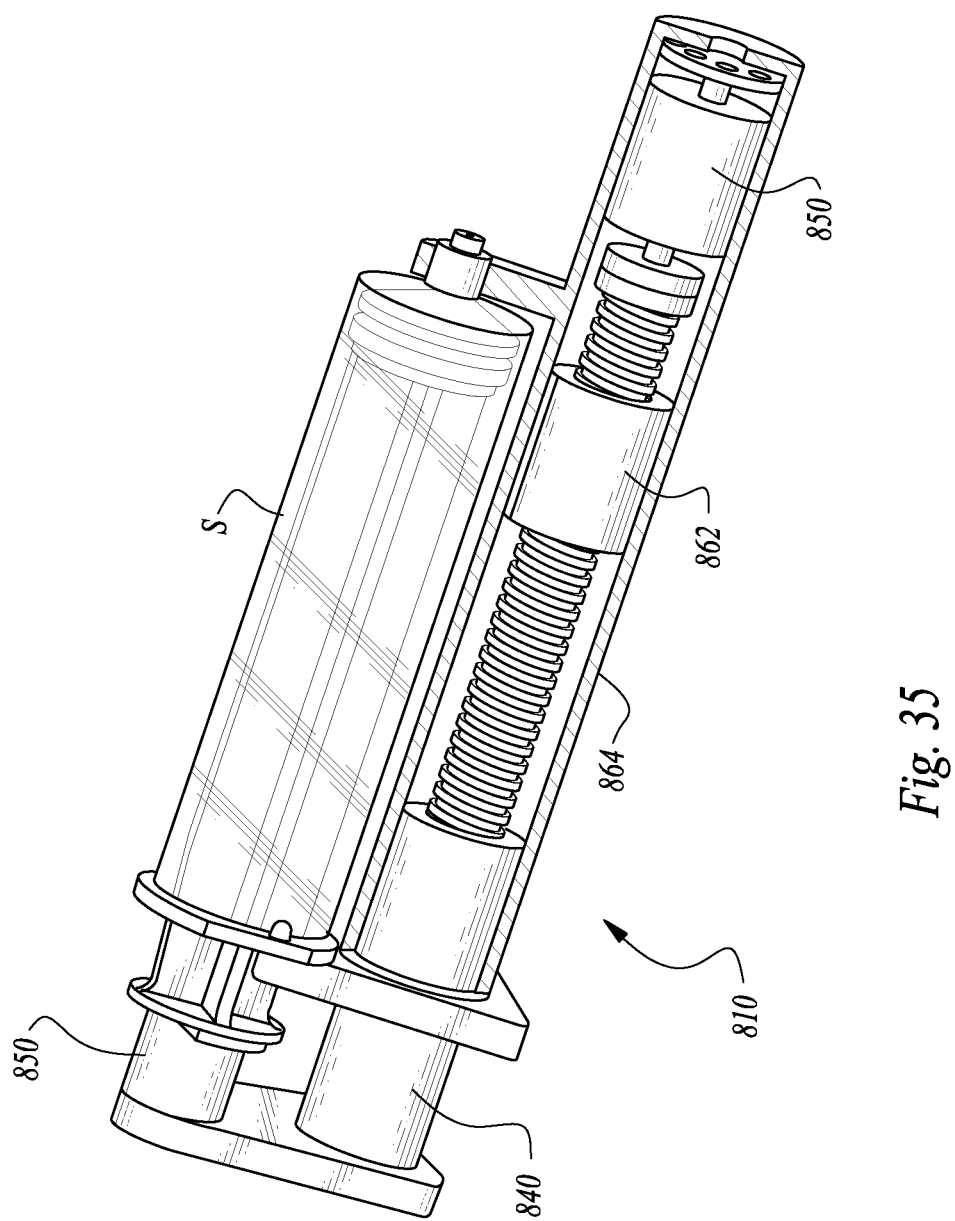
FIG. 35 is a perspective view of an alternative embodiment motorized infuser and syringe.

With particular reference to FIG. 35 details of a motorized infuser 810 embodiment of this invention are described. With the motorized infuser 810, a housing which would otherwise have been filled with gas (or containing a vacuum) is fitted with a motor 860, such as at a distal end, with a rotating output shaft. This rotating output shaft is preferably coupled to an elongate threaded shaft 864. A threaded nut 862 is configured to ride along this threaded shaft 864 with threads which mate with the threaded shaft 864 to cause the nut 862 to translate when the threaded shaft 864 rotates. An arm 840 of the infuser 810 is coupled to the nut 862 (with portions of this arm 840 cut away in FIG. 15 to reveal details of the threaded shaft 864).

A driver 850 is coupled to the arm 840 and acts upon a plunger of the syringe S. Thus, when the motor 860 rotates, the threaded shaft 864 rotates, causing the nut 862 to translate and the arm 840 coupled to the nut 862 is also caused to translate so that the driver 850 acts on the plunger of the syringe S to infuse fluid from the syringe S. Typically, some form of guide is provided on the nut 862 to keep the nut 862 from rotating with the threaded shaft 864, so that the nut 862 is required to translate when the threaded shaft 864 rotates.

A controller would be provided for the motor 860 which would keep track of a rate of rotation and match a rate of rotation and a rate of translation of the nut 862 to match a rate of infusion desired for the syringe S. Such a controller could be adjustable with inputs to allow medical professionals to set and adjust a rate of infusion associated with the motor 860. The motor 860 would also require some form of power source to provide motive force for operation of the motor 860. Such a power source could be batteries, a self contained power source such as fuel cells or solar panels, or could be an electric cord which can plug into available standard electric service.

Other forms of springs or resilient members could also be interposed between the arm 440 and other portions of the infuser 410 to provide the resistance force energizer of this invention to cause the driver 450 to apply forces on the plunger P of the syringe S.

Figure 20:
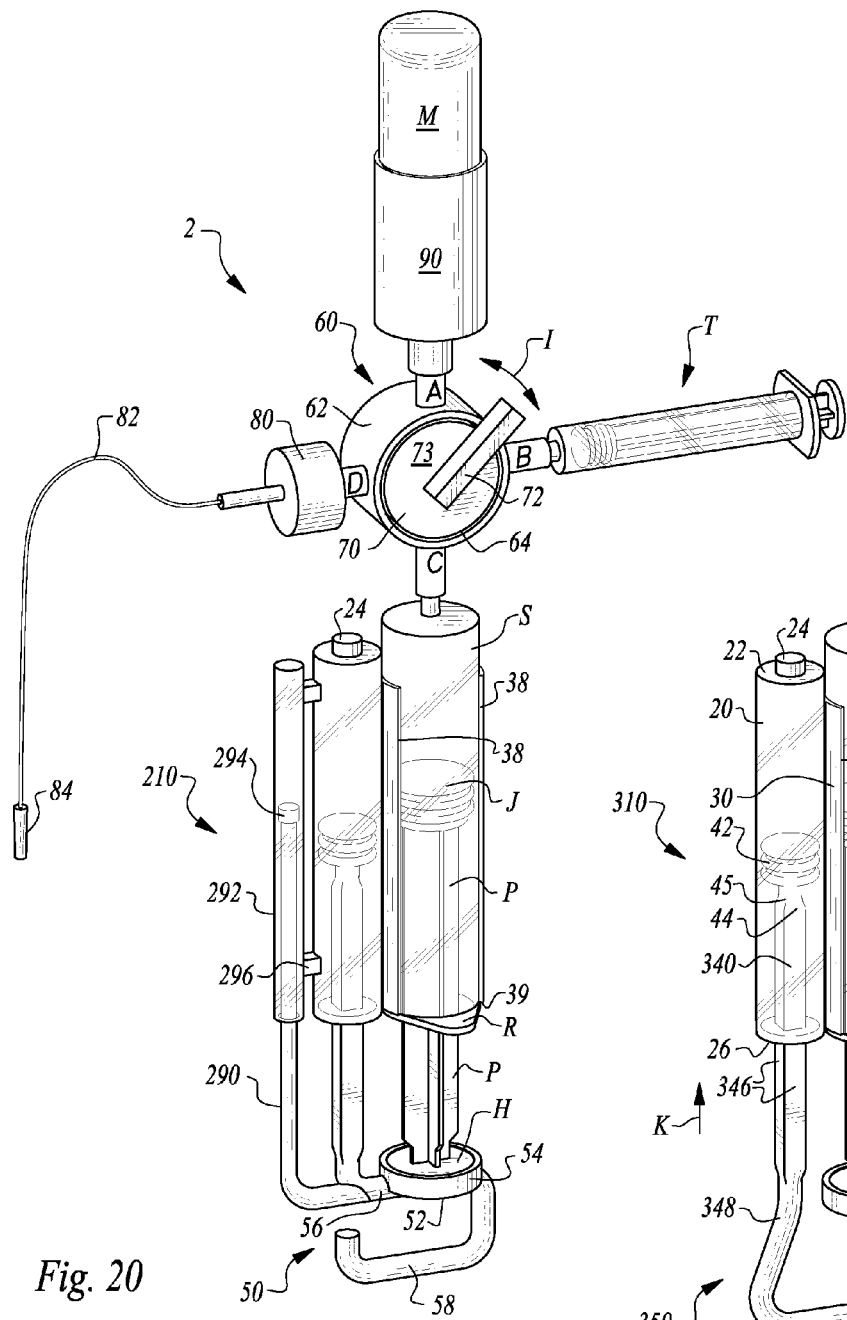
FIG. 20 is a perspective view similar to FIG. 7, but with a dampening system shown consisting of a dampening cylinder attached to the infusion device body and a dampening rod attached to the force activator section (force activator is equivalent to the arm and driver together). The dampening system becomes active by allowing interaction of the cylinder and rod when the infusion device interacts with the syringe during infusion and allows infuser incursion at a controlled, desired infusion rate. The dampening system components (cylinder and rod) may be reversed with respect to their location.

FIG. 20 is a perspective view similar to FIG. 7, but with a dampening system 210 shown consisting of a dampening cylinder 292 attached to the infusion device body through a pair of supports 296 and a dampening rod 290 (terminating at a seal 294) attached to the force activator section 56 (force activator is equivalent to the arm and driver together). The dampening system 210 becomes active by allowing interaction of the cylinder 292 and rod 290 when the infusion device interacts with the syringe S during infusion and allows infuser incursion at a controlled, desired infusion rate. The dampening system 210 components (cylinder 292 and rod 290) may be reversed with respect to their location.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A non-electric system for medicament infusion, the system comprising:

at least one infusion device adapted to be coupled lateral to at least one medicament syringe;

said medicament syringe including a cylinder and an elongate plunger assembly, said assembly comprised of an actuating rod with a distally positioned piston opposite a proximal terminus, said piston adapted to sealingly slide within said cylinder, said cylinder including a distal cylinder portion positioned distal to said piston, said distal cylinder capable of containing medicament and having at least one fluid conveyance port communicating with said distal cylinder portion;

said infusion device comprising a body, a resistance force energizer, and a force applicator, said force applicator including a reciprocating arm with a driver at a proximal end, said resistance force energizer applying a force between said body and said force applicator to move said force applicator toward a resting point;

said driver including a thrust surface and a handle, said handle adapted for manual excursion of said force applicator against said resistance force energizer and away from said resting point of said force applicator, said excursion requiring manual input of energy to overcome said force applied by said resistance force energizer; wherein said force applicator is adapted to undergo said excursion along a path avoiding engagement with said syringe proximal terminus and to then be rotated to align with and engage with said syringe proximal terminus; said driver adapted to be selectively engaged or disengaged with said syringe proximal terminus at said driver thrust surface;

and said driver, when engaged with said syringe proximal terminus, adapted to transfer forces from said force applicator to said syringe plunger assembly, thereby pushing said syringe piston distally into said syringe distal cylinder portion, forcing medicament efflux through said fluid conveyance port.

2. The system of claim 1 wherein said resistance force energizer contains a vacuum chamber, said vacuum chamber having at least one distal atmospheric port and a sealingly slidable piston having a distal side and a proximal side, said distal side forming a proximal wall of said vacuum chamber and said proximal side exposed to the atmosphere and attached to said force applicator reciprocating arm, said distal atmospheric port having a fluid tight means for closure adapted to open and close said distal atmospheric port, thereby allowing gas evacuation from said vacuum chamber if the vacuum condition has been compromised.

3. The system of claim 1 wherein said force applicator is adapted to be reversibly disabled in a state storing potential energy.

4. The system of claim 1 wherein said force applicator reciprocating arm is oriented to traverse through an alignment guide provided with said infusion device as said arm reciprocates, said arm having long segments thereof with a cross-section matching a corresponding cross-section of said alignment guide thereby disallowing rotation of said force applicator and short segments thereof which have a cross-sectional width less than the narrowest width of said alignment guide thereby allowing rotation of said force applicator, such that said arm can be rotated relative to said alignment guide at said short segments of said arm and not rotated relative to said alignment guide at said long segments of said arm.

5. The system of claim 1 wherein said force applicator reciprocating arm is oriented to traverse through an alignment guide attached to said infusion device body, said arm including a plurality of facets on portions thereof and said alignment guide is provided with facets matching and corresponding to a cross-section of said arm where said facets are located, and with a portion of said arm in the form of a neck having a circular cross-section with a diameter less than a minimum width of said alignment guide, such that when said cylindrical neck of said arm is aligned with said alignment guide, said arm can rotate freely about a long axis thereof, but with said arm only able to translate linearly through said alignment guide in some specific rotational orientations where said arm facets and said alignment guide facets are matching and corresponding.

6. The system of claim 1 wherein said force applicator reciprocating arm is oriented to traverse through an alignment guide provided with said infusion device as said arm reciprocates, wherein said force applicator arm includes facets thereon and with said alignment guide having facets matching and mating with a cross-section of said arm, said facets of said arm spaced apart by edges, said edges sufficiently wide to resist passage through said alignment guide when said edges are rotated out of alignment with facets of said alignment guide.

7. The system of claim 6 wherein said arm can be rotated to a holding position where it resists incursion and stores potential energy and then repositioned to a non-holding position with said facets of said arm aligned with facets of said alignment guide to allow said incursion.

8. The system of claim 1 wherein said driver thrust surface includes a plate adapted to engage said syringe proximal terminus, said plate having a distally protruding rim around a portion of its perimeter to encompass a similar portion of said syringe proximal terminus and thereby resist lateral movement of said syringe proximal terminus at said plate.

9. The system of claim 4 wherein said force applicator arm is adapted to undergo said excursion along a long segment path with said driver in a non rotatable but translatable first position whereas an engaged state is avoided, following which at a position of substantially full excursion said arm is adapted to be rotated at said short segments such that said driver rotates about an axis parallel with said excursion and into a second position adapted to allow said driver to begin incursion and to become engaged with said syringe proximal terminus, said incursion occurring along said long segment in a non rotatable but translatable said second position, thereby disallowing any rotation of said arm during said incursion.

10. The infusion device of claim 1 wherein said reciprocating arm has faceted sides such that said arm exhibits a faceted cross-section perpendicular to a long axis of said arm, said arm translating through a correspondingly faceted alignment guide affixed to said body of said infusion device, said arm including at least one neck on a portion thereof, said neck having a width smaller than the narrowest diameter of said faceted alignment guide, such that when said neck is aligned with said faceted alignment guide, said arm can rotate freely, but when said faceted portion of said arm is adjacent said faceted alignment guide, said arm is restrained from rotation.

11. The system of claim 1 wherein said infusion device has an attachment device for attaching said infusion device to living and inanimate objects.

12. The system of claim 11 wherein said attachment device includes a self connecting type strap.

13. The system of claim 1 wherein said medicament syringe is removably coupleable to said infusion device.

14. The system of claim 13 wherein said infusion device is reusable and said medicament syringe is disposable.

15. The system of claim 1 wherein said infusion device and said syringe are unified and disposable.

16. The infusion device of claim 1 wherein said infusion device includes a dampening system, said dampening system including a fluid filled dampening cylinder attached rigidly and in parallel to said infusion device body and a dampening rod attached rigidly and in parallel to said force applicator, said dampening cylinder adapted to receive said dampening rod during which said dampening system becomes activated, said activated dampening system adapted to limit the speed of incursion thereby limiting the rate of infusion.

17. At least one nonelectric infusion device removably coupleable to at least one medical syringe, said device adapted to infuse medicament from the syringe, the syringe having a cylinder with a fluid conveyance port, an open end opposite the fluid conveyance port, an elongate plunger assembly with a distal piston opposite a proximal terminus, and the piston adapted to sealingly slide within the cylinder; the infusion device comprising in combination:
a body containing a resistance force energizer;
a force applicator including an arm;
said arm having a free end adjacent the resistance force energizer; wherein said arm is adapted to be rotated, said arm including a plate on an end thereof opposite said sliding sealed piston, said plate adapted to engage the proximal terminus of the syringe in less than all rotational positions for said arm; said force applicator adapted to be removably coupleable to the proximal terminus of the syringe at a location spaced from said free end of said arm;
said force applicator adapted to be removably coupleable to the proximal terminus of the syringe at a location spaced from said free end of said arm;
said force applicator including a thrust surface and a handle which is hand grippable when at a resting point for manual excursion of said force applicator against said resistance force energizer and away from said resting point of said force applicator, said excursion requiring manual input of energy to overcome said force applied by said resistance force energizer;
said driver adapted to be selectively engaged or disengaged with said syringe proximal terminus at said driver thrust surface;
said driver, when engaged with said syringe proximal terminus, adapted to transfer forces from said force applicator to said syringe plunger assembly, thereby pushing said syringe piston distally into said syringe distal cylinder portion, forcing medicament efflux through said fluid conveyance port;
and said infusion device body having an attached clamp, said clamp having an elongate inside wall with a diameter substantially similar to a diameter of the syringe cylinder, said clamp having an elongate lateral opening between opposite edges sufficiently large to allow said clamp to snap over and surround a portion of the syringe thereby inhibiting syringe rotation or motion perpendicular to the syringe long axis, the syringe including a ledge adjacent the open end where the cylinder of the syringe exhibits increased diameter, said clamp adapted to abut one or more sides of said ledge and hold the syringe from movement along the syringe long axis thereof when the syringe plunger assembly is being moved by the force applicator or the fingers of the user and said clamp has been snapped onto the cylinder of the syringe with said clamp abutting the ledge of the syringe.

18. The system of claim 17 wherein said infusion device is reusable and said medicament syringe is disposable.

19. The infusion device of claim 17 wherein said resistance force energizer includes a vacuum chamber, said vacuum chamber including a sliding sealed piston forming a wall of said vacuum chamber, and said free end of said arm coupled to said sliding sealed piston.

20. The infusion device of claim 17 wherein said arm has faceted sides such that said arm exhibits a faceted cross-section perpendicular to a long axis of said arm, said arm translating through a correspondingly faceted alignment guide affixed to the infusion device body, said arm including at least one neck on a portion thereof, said neck having a width smaller than the narrowest diameter of said faceted alignment guide such that when said neck is aligned with said faceted alignment guide, said arm can rotate freely, but when said faceted portion of said arm is adjacent said faceted alignment guide, said arm is restrained from rotation.

21. The infusion device of claim 17 wherein said plate includes a rim extending from a periphery thereof, said rim adapted to at least partially surround the proximal terminus of the syringe plunger assembly when the proximal terminus of the syringe is adjacent said plate, such that said rim resists said plunger assembly movement relative to said plate when said plunger assembly proximal terminus is adjacent said plate.

22. The infusion device of claim 17 wherein said infusion device includes a dampening system, said dampening system including a fluid filled dampening cylinder attached rigidly and in parallel to said infusion device body and a dampening rod attached rigidly and in parallel to said force applicator, said dampening cylinder adapted to receive said dampening rod during which said dampening system becomes activated, said activated dampening system adapted to limit the inward speed of said force applicator when coupled to said syringe plunger assembly thereby limiting the rate of infusion.

23. A system for infusing of fluid from a syringe, the syringe having a fluid containing cylinder, an outlet from the cylinder and a plunger adapted to translate into the cylinder to push fluid from the syringe through the outlet, the system comprising in combination:
a driver coupled to the plunger;
a resistance force energizer interposed between said driver and the cylinder of the syringe, such that the resistance force energizer exerts a force on said driver pushing the plunger into the cylinder to efflux fluid from the outlet of the cylinder of the syringe;
said driver including a thrust surface and a handle which is hand grippable when at a resting point for manual excursion of said driver against said resistance force energizer and away from said resting point of said driver, said excursion requiring manual input of energy to overcome said force applied by said resistance force energizer;
said driver adapted to be selectively engaged or disengaged with said syringe proximal terminus at said driver thrust surface by rotation of said driver thrust surface into and out of engagement with said syringe proximal terminus; and said driver, when engaged with said syringe proximal terminus, adapted to transfer forces from said piston to said syringe plunger, thereby pushing said syringe piston distally into said syringe distal cylinder portion, forcing medicament efflux through said fluid conveyance port.

24. The system of claim 23 wherein said resistance force energizer includes an elongate vacuum chamber with a movable piston residing therein, an arm coupled to said piston, said arm coupled to said driver, said vacuum chamber coupled to the cylinder of the syringe.

25. A system for infusing of fluid from a syringe, the syringe having a fluid containing cylinder, an outlet from the cylinder and a plunger adapted to translate into the cylinder to push fluid from the syringe through the outlet, the system comprising in combination:

a driver coupled to the plunger;

an elongate vacuum chamber with a movable piston residing therein, an arm coupled to said piston, said arm coupled to said driver, said vacuum chamber coupled to the cylinder of the syringe, such that said arm exerts a force on said driver pushing the plunger into the cylinder to efflux fluid from the outlet of the cylinder of the syringe;

said driver including a thrust surface and a handle which is hand grippable when at a resting point for manual excursion of said driver against said resistance force energizer and away from said resting point of said driver, said excursion requiring manual input of energy to overcome said force applied by said resistance force energizer;

said driver adapted to be selectively engaged or disengaged with said syringe proximal terminus at said driver thrust surface by rotation of said driver thrust surface into and out of engagement with said syringe proximal terminus; and said driver, when engaged with said syringe proximal terminus, adapted to transfer forces from said piston to said syringe plunger, thereby pushing said syringe piston distally into said syringe distal cylinder portion, forcing medicament efflux through said fluid conveyance port.

26. The system of claim 1 wherein said handle is hand grippable when at said resting point.

27. The system of claim 1 wherein said driver is disengaged with said syringe proximal terminus while said resistance force energizer stores energy for later transfer to said syringe proximal terminus when said driver is engaged.

* * * * *